(12) United States Patent
Mizutani et al.

(10) Patent No.: US 7,033,342 B2
(45) Date of Patent: Apr. 25, 2006

(54) FLAP-EQUIPPED INTERLABIAL PAD

(75) Inventors: Satoshi Mizutani, Kagawa (JP); Koichi Yamaki, Kagawa (JP); Yuki Noda, Kagawa (JP); Megumi Tokumoto, Kagawa (JP); Akane Sakai, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 10/705,670

(22) Filed: Nov. 10, 2003

(65) Prior Publication Data

US 2004/0158221 A1    Aug. 12, 2004

Related U.S. Application Data

(63) Continuation of application No. PCT/JP02/04896, filed on May 21, 2002.

(51) Int. Cl.
*A61F 13/15* (2006.01)
*A61F 13/56* (2006.01)

(52) U.S. Cl. .......................... 604/385.02; 604/385.17; 604/385.03; 604/386

(58) Field of Classification Search ........... 604/385.17, 604/385.04
See application file for complete search history.

(56) References Cited

U.S. PATENT DOCUMENTS

| | | | |
|---|---|---|---|
| 4,595,392 A * | 6/1986 | Johnson et al. | 604/385.17 |
| 5,658,270 A | 8/1997 | Lichstein | |
| 5,885,265 A * | 3/1999 | Osborn et al. | 604/367 |
| 6,015,934 A * | 1/2000 | Lee et al. | 604/358 |
| 6,350,258 B1 * | 2/2002 | Markowiecki | 604/385.201 |
| 6,461,340 B1 * | 10/2002 | Lenker et al. | 604/385.17 |
| 2004/0002686 A1 * | 1/2004 | Glasgow et al. | 604/300 |

FOREIGN PATENT DOCUMENTS

| | | |
|---|---|---|
| TW | 247431 A1 | 5/1995 |
| TW | 294591 A1 | 1/1997 |
| TW | 338315 A1 | 8/1998 |
| TW | 362966 A1 | 7/1999 |
| TW | 386030 A1 | 4/2000 |
| TW | 394681 A1 | 6/2000 |
| TW | 416847 A1 | 1/2001 |
| TW | 442278 A1 | 6/2001 |

(Continued)

OTHER PUBLICATIONS

Mizutani, et al., "Interlabial Pad and Package Thereof", U.S. Appl. No. 10/705,810, filed Nov. 10, 2003.

(Continued)

*Primary Examiner*—Tatyana Zalukaeva
*Assistant Examiner*—Keisha Gibson
(74) *Attorney, Agent, or Firm*—Darby & Darby

(57) ABSTRACT

An interlabial pad to be fitted to the labia providing an interlabial pad with flap portions that can maintain the retention state in the interlabial space irrespective of the quantity of body fluid discharge such as menstrual blood. A mini-sheet piece (3) is attached to the opposite side face to the body side face (2*b*) of the interlabial pad (2) in such a way that a pad of it protrudes from both side edges of the interlabial pad (2) forming flap portions (4A) and (4B). Adhesives (6A) and (6B) are applied to the body side face of the flap portions (4A) and (4B). The interlabial pad (2) is retained in the interlabial space and the flap portions (4A) and (4B) are affixed to the surface of the labia majora to fit the interlabial pad with the flap portions (1).

2 Claims, 18 Drawing Sheets

FOREIGN PATENT DOCUMENTS

| | | |
|---|---|---|
| TW | 450802 A1 | 8/2001 |
| TW | 454503 A1 | 9/2001 |
| TW | 470640 A1 | 1/2002 |
| TW | 524677 A1 | 3/2003 |
| WO | WO-98/08475 A1 | 3/1998 |
| WO | WO-98/25561 A1 | 6/1998 |
| WO | WO 9825561 A1 * | 6/1998 |
| WO | WO-98/57610 A1 | 12/1998 |
| WO | WO-99/01093 A1 | 1/1999 |
| WO | WO-99/01094 A1 | 1/1999 |
| WO | WO-99/01096 A1 | 1/1999 |
| WO | WO 9901093 A1 * | 1/1999 |
| WO | WO-99/26575 A1 | 6/1999 |
| WO | WO 9926575 A1 * | 6/1999 |
| WO | WO-99/55272 A1 | 11/1999 |
| WO | WO-99/56689 A1 | 11/1999 |
| WO | WO-00/40197 A1 | 7/2000 |

OTHER PUBLICATIONS

Mizutani, et al., "Interlabial Pad", U.S. Appl. No. 10/705,406, filed Nov. 10, 2003.

Mizutani, et al., "Interlabial Pad", U.S. Appl. No. 10/705,408, Nov. 10, 2003.

Mizutani, et al., "Interlabial Pad Individual Packaging Vessel", U.S. Appl. No. 10/705,673, Nov. 10, 2003.

Mizutani, et al., "Interlabial Pad", U.S. Appl. No. 10/705,780, Nov. 10, 2003.

Mizutani, et al., "Interlabial Pad", U.S. Appl. No. 10/705,778, Nov. 10, 2003.

Mizutani, et al., "Interlabial Pad and Package Thereof", U.S. Appl. No. 10/705,404, Nov. 10, 2003.

Mizutani, et al., "Interlabial Pad and Package Thereof", U.S. Appl. No. 10/705,400, Nov. 10, 2003.

Mizutani, et al, "Interlabial Pad and Package", U.S. Appl. No. 10/706,303, Nov. 10, 2003.

Mizutani, et al., "Interlabial Pad Individual Packaging Body", U.S. Appl. No. 10/705,669, filed Nov. 10, 2003.

Mizutani, et al., "Interlabial Pad", U.S. Appl. No. 10/705,407, filed Nov. 10, 2003.

Mizutani, et al., "Interlabial Pad", U.S. Appl. No. 10/705,811, filed Nov. 10, 2003.

Mizutani, et al., "Interlabial Pad", U.S. Appl. No. 10/705,403, filed Nov. 10, 2003.

Mizutani, et al., "Individual Packaging Body and Outer Vessel Therefor", U.S. Appl. No. 10/705,402, filed Nov. 10, 2003.

Mizutani, et al., "Interlabial Pad", U.S. Appl. No. 10/705,399, filed Nov. 10, 2003.

Mizutani, et al., "Interlabial Pad Individual Packaging Vessel, and Individual Packaging Body", U.S. Appl. No. 10/705,781, filed Nov. 10, 2003.

European Search Report for EP 02 77 1756 completed on Nov. 17, 2004.

Mizutani, et al., "Interlabial Pad", U.S. Appl. No. 10/705,812, filed Nov. 10, 2003.

Mizutani, Satoshi, "Interlabial Product Having Form for Finger Securement, and Individual Package", U.S. Appl. No. 10/705,779, filed Nov. 10, 2003.

* cited by examiner (A)

(B)

(A)

(B)

(C)

(D)

(E)

(A)

(B)

(C)

(D)

(A)

↓

(B)

(A)

(B)

(C)

(A)

(B)

(C)

(A)

(B)

(A)

(B)

(C)

(A)

(B)

FLAP-EQUIPPED INTERLABIAL PAD

CROSS-REFERENCE TO RELATED APPLICATIONS

This application is a Continuation of International Application No. PCT/JP02/04896 filed May 21, 2002, which application published in Japanese on Nov. 28, 2002 as WO 02/094160 A1 under PCT Article 21(2).

BACKGROUND OF THE INVENTION

1. Technical Field

The present invention relates to an interlabial pad fitted on female's labia

2. Background Art

Conventionally, sheet type absorbent products like a sanitary napkin are used generally as female sanitary products to absorb body fluid such as menstrual blood. Here, there have been great efforts to prevent the leak of menstrual blood from a gap caused by poor adhesion near the ostium vaginae as for the sanitary napkin.

However, since the sanitary napkin, used by being fixed to clothes, has. intrinsically poor adhesion near the ostium vaginae, position shift may occur between the underwear to which the sanitary napkin is fixed and the inner thigh due to the body action of the wearer, and an unnecessary gap generates sometimes.

Under such situation, sanitary products, of the interlabial pad have attracted people as a sanitary product smaller than the sanitary napkin in recent years.

The interlabial pad is used by inserting its portion between the labia and bringing it into contact with the inner face of labia, it prevents the menstrual blood from leaking because of higher adhesion to the body than that of the sanitary napkin, and the menstrual blood from bringing widely into contact with the body by diffusing, so it is sanitary and clean. Moreover, it has advantages that it excels in a feeling of wearing and is comfortable because of being smaller than the sanitary napkin.

As used herein, the term "interlabial pad" refers to the item first fitted to the interlabial space (in between the labia), and then retained in the labia with the pinching force of the labia themselves. If it absorbs a large amount of menstrual blood, the fixing position may be displaced due to its own weight, and in the worst cases, it may fall off from the inside of the labia. In this case, the function to fit the interlabial pad to body does not work sufficiently, and even menstrual blood leaks.

The present invention has been worked out in view of the shortcoming in the prior art as set forth above. It is an object of the present invention to provide an interlabial pad that can stay in the labia irrespective of quantity of body fluid such as menstrual blood.

DISCLOSURE OF THE INVENTION

In order to achieve the task shown above, the interlabial pad according to the present invention has the flap portions, which can cover at least the labia majora at both side edges and can be fixed to the skin of the wearer.

More specifically, the present invention provides the items shown below.

(1) An interlabial pad having an appropriate size to contain an absorbent body which can absorb body fluid and to be pinched in interlabial space without forcing, the interlabial pad comprising a pair of flap portions at each side edge portion of both sides of the interlabial pad which cover labia majora when the interlabial pad is worn, the flap portion being provided with an adhesive portion on a skin contact face which contacts a skin of a wearer.

The interlabial pad according to the present invention has a flap portion at each of both side edges. So, when the wearer fits the interlabial pad to the interlabial space (in between the labia), the flap portion is not inserted in the interlabial space; but it is exposed to the outside of the labia. The flap portion is provided with an adhesive area that can adhere to skin. It is possible to arrange the flap portion to cover the labia majora sandwiching the interlabial pad such that the flap portion contacts closely with or sticks to the outer wall of the labia majora and farther a skin surface beyond the outer wall of the labia majora. By this, the interlabial pad is retained in the original position without being displaced between the labia even when the pad is in a high humid and wet condition since the pad retaining condition is strengthened.

In this respect, Japanese Patent Publication No. Hei. 6-506368 discloses an incontinence pad for wearing in the interlabial space, where an adhesive is applied to the side contacting the inner wall of the labia. With this incontinence pad, it can be supposed that it can retain body fluid such as urine absorbed with the applied adhesives in the labia.

However, when comparatively large amount of body fluid is discharged, it is highly likely that the body fluid enter the bonding interface where the adhesive and the inner surface of the labia touch to each other. In this case, the tacking strength of the adhesive is lowered to deteriorate the close contact of adhesion between the incontinence pad and the labia. Especially, in the case that urine is discharged all at once from the urinary duct such as abdominal pressure urinary incontinence, the incontinence pad is likely to fall off from the labia due to the momentum of the urine gushed out.

In addition, it is possible that the elution component generated when the adhesive contacts body fluid gives chemical stimulus to the wearer's labia mucosa. In this case, some wearers may develop allergy reactions.

On the other hand, the adhesive portion of the interlabial pad according to the present invention, which is formed by applying an adhesive to fix the interlabial pad, is positioned outside of the labia through the intermediary of the flap portion, not at the inner face of the labia. So, body fluid does not touch the adhesive and the tacking strength is maintained while securing safety of wearers.

Application pattern of the adhesive on the adhesive portion is not particularly limited as long as the adhesive is not removed when the interlabial pad is worn and excessive pains to the wearer are not caused when the interlabial pad is removed. Application patterns are selectable from planar pattern, dot pattern, grid pattern, stripe pattern, etc.

Further, application area of the adhesive on each flap portion is at least 5 $mm^2$, more preferably 10 to 200 $mm^2$, further preferably 25 to 80 $mm^2$. Furthermore, if the adhesive is applied with the range of area shown above, the adhesive having the tack strength described in (11) is preferably used.

(2) The interlabial pad according to (1), wherein the pair of flap portions is provided at a part of each side edge portion of both sides of the interlabial pad or almost all parts of each side edge portion of both sides of the interlabial pad.

In the interlabial pad with the flap portions according to the present invention, each flap portion is provided at each side edge portion, whose longitudinal length is shorter than or almost the same as that of the side edge.

In this respect, if each longitudinal length of the pair of flap portions is shorter than that of the side edge of the interlabial pad, the operation to wear or remove the pad is easily performed. On the other hand, if the longitudinal length of the flap portion is almost same as that of the side edge of the interlabial pad, the retaining force of the interlabial pad between the labia is further strengthened since the flap portion covers the whole labia majora. As shown above, the effect can change depending on the size of the flap portion.

If the flap portions are provided at almost whole area of both side edges of the interlabial pad, the adhesive portion is preferably 50 to 80% of the total length of the flap portion and blank margins are preferably provided at the front and rear area. By this, it is possible for the wearer to remove the flap portions easily by pinching a part of the flap portions affixed to the wearer's skin when the interlabial pad having the flap portions is replaced so that the removal characteristics of the interlabial pad with the flap portions is improved.

(3) The interlabial pad according to (1) or (2), wherein the pair of flap portions comprises a plurality of pairs of flap portions at each side edge portion of the interlabial pad.

In the interlabial pad with the flap portions according to the present invention, a plurality of flap portions are provided on each side edge portion. For example, it is possible to provide two pairs of flap portions at two (front and rear) parts of both side edge portions of the interlabial pad, respectively (see FIG. 16(B)).

Thus, if the plurality of pairs of flap portions are provided, the retention of the interlabial pad between the labia is improved as well as the load applied to the flap portions is dispersed and the wearer's various actions in wearing may be supported so that the interlabial pad is hardly removed from the interlabial space.

As used herein, the term "front side" of the interlabial pad according to the present invention refers to the region that is positioned near clitoris, and "rear side" refers to the region that is positioned near perineum when worn.

(4) The interlabial pad according to any one from (1) to (3), wherein the pair of flap portions is provided at the position biased towards either end portion in the longitudinal direction of the interlabial pad.

In the interlabial pad with the flap portions according to the present invention, the pair of flap portions may be provided at a position closer to either the front end or the rear end, but not in the center region.

With regard to growth types of the labia, it is generally said that the front side growth type is 60%, that the equal growth type is 20%, and that the rear side growth type is 20%. Among them, for example, the interlabial pad is likely to be held near the front side by the wearer of the front side growth type.

So, near the ostium vaginae as a discharge opening, retaining force of the interlabial pad is so weak that a close contact or sufficient adhesion to prevent leakage may not be obtained. In order to prevent this, it is effective to provide the flap portions placed in the rear side of the interlabial pad for the wearer having the labia shape of front side growth type.

As this, in the present invention, individual differences in growth type of the labia can be supported by changing the position of the flap portions.

(5) The interlabial pad according to any one from (1) to (4), wherein the flap portions have extensibility in at least one part.

In the interlabial pad with the flap portions of the present invention, the flap portions are extensible. So, even if the own weight exceeds the pinching force as the interlabial pad has absorbed a large amount of body fluid, extensible tensile force resists the own weight of the interlabial pad to maintain the contact.

As used herein, the term "at least one part" refers to the state the interlabial pad has extensibility at the whole or one part of the flap portions.

"In the case of having extensibility in one part", for example, refers to the state that extensibility is provided in an inner side between the side edge of the interlabial pad and the adhesive portion provided on the flap portions. Since extensibility is provided in such range, the flap portions can easily shift themselves in shape to follow according to various actions of the wearer when the interlabial pad is worn. So, the interlabial pad can stay at the fixed position of the interlabial-space, furthermore, the part of the adhesive portion affixed to the skin may not pull the skin excessively by adhesion between them so that the wearer may have a comfortable wear feeling.

Extensibility may exist only in the lateral direction as well as both in the longitudinal and lateral directions. Extensibility in the lateral direction may provide contacting or adhesive force to the interlabial pad.

Furthermore, in the present invention, materials usable for the flap portions include the material that has originally extensibility and the material that does not have extensibility originally and has acquired extensibility later.

(6) The interlabial pad according to any one from (1) to (5), the pad comprising:

a water-permeable surface side sheet provided on a body side face; and a water-impermeable back side sheet provided on an opposite side face to the body side face, wherein the flap portions are composed of an extended part of the water-permeable surface side sheet, an extended part of the water-impermeable back side sheet, or equally extended parts of both the water-permeable surface side sheet and the water-impermeable back side sheet.

In the interlabial pad with the flap portions according to the present invention, the flap portions are formed by partially extending the component materials of the interlabial pad main body.

In this case, when the flap portions are formed at the extended region of the water-permeable surface side sheet, which is positioned at a body side of the interlabial pad, it is possible to minimize the skin area stained by body fluid even if body fluid leaks from around the side edges of the interlabial pad. In addition to that, when the flap portion is formed at the extended region of the water-impermeable back side sheet, which is positioned at the opposite side to the body side, it is possible to prevent body fluid from soiling undergarments even if body fluid leaks from around the side edges of the interlabial pad. Further, the flap portions are formed by extending both the surface side sheet and the back side sheet, both functions shown above may be provided.

(7) The interlabial pad according to any one from (1) to (6), the pad comprising a mini-sheet piece which forms a finger insertion opening having a finger breadth opening secured and a finger insertion space continuing therefrom, wherein the mini-sheet piece is attached to the opposite side face to the body side face of the interlabial pad.

In the interlabial pad with the flap portions according to the present invention, the mini-sheet piece is attached to the opposite side face to the body side face of the interlabial pad in such a way that the finger insertion opening with the fingerbreadth opening is formed. Specifically, an opening is formed between one sleeve side of the mini-sheet piece and the opposite side face to the body side face of the interlabial pad which are non-bonded, since at least one of both sleeve portions of the mini-sheet piece is not bonded to the opposite side face to the body side face of the interlabial pad in the lateral direction of the opposite side face to the body side face of the interlabial pad. Such a sleeve opening turns to be the finger insertion opening in which a finger can be inserted (see FIG. 10).

The mini-sheet piece is bonded to the interlabial pad at the both edges along the longitudinal direction. That is, the mini-sheet piece is bonded on the opposite side face to the body side face of the interlabial pad by striding from one edge to the other edge. The region inside between the left and right side portions is not bonded (not glued). So, space (the finger inserting space) in which a finger can be inserted and retained is formed in the region where the mini-sheet piece strides from the one side portion to the other side portion. By this, the finger can be inserted from the finger insertion opening to the finger insertion space in such a way that the finger cushion touches the opposite side face to the body side face of the interlabial pad.

Here, the interlabial pad is fixed to the interlabial space that can hardly be observed. So, in some cases, the wearer cannot detect the appropriate fixing point immediately and should repeat fixing procedures. In addition, if the interlabial pad is not fixed to the appropriate point, it may be caused that a close contact between the labia and the pad cannot be established so as to cause leakage of menstrual blood. Further, since the pad is smaller than the sanitary napkin, damages due to menstrual blood leakage are likely to be large.

In this respect, PCT International Publication No. WO99/56689 discloses an interlabial pad that has a projection formed on the opposite side of to the body side. With this structure, a wearer can fix the pad by pinching and holding the projection between fingers. It is supposed that this kind of pad can be fixed more readily than a pad without a projection. (see FIG. 27)

With this structure, a wearer has to detect the fixing point with her intuition since the detection is made by her nail tips. It is also hard to tightly press the interlabial pad to the pubic region just by pinching the projection.

On the other hand, since it is possible to hold the interlabial pad at the fingertip by inserting the finger into the finger insertion opening provided in the interlabial pad with the flap portions according to the present invention, the wearer, detecting the right fixing point by finger sense, can fix the interlabial pad on the appropriate position even if it is the interlabial space that is hardly observed.

(8) The interlabial pad according to any one from (1) to (5), wherein the mini-sheet piece having a length dimension longer than a lateral dimension of the interlabial pad is attached on the opposite side face to the body side face of the interlabial pad by crossing the interlabial pad in the lateral direction, and wherein the pair of flap portions is formed by protrusion parts of the mini-sheet piece protruding from both side edges of the interlabial pad in the longitudinal direction.

In the interlabial pad with the flap portions according to the present invention, the flap portion is formed only by the structure attaching the mini-sheet piece. So, it is possible to manufacture the interlabial pad with improved gripping force between the labia just by adding a process of attaching the mini-sheet piece to the existing series of processes to manufacture the ordinary interlabial pad that does not have such flap portions.

(9) The interlabial pad according to (8), wherein the mini-sheet piece forms the finger insertion opening having the fingerbreadth opening and the finger inserting space continuing therefrom between the mini-sheet piece and the opposite side face to the body side face of the interlabial pad.

In the interlabial pad with the flap portions according to the present invention, the mini-sheet piece attached to the opposite side face to the body side face functions as the flap portions and the finger inserting portion. This provides the interlabial pad with superb functionality with a simple construction without equipping it with two functions separately.

In this case, the bonding portion between the mini-sheet piece and the interlabial pad is provided near both side edges of the interlabial pad so that the finger insertion opening having the fingerbreadth is secured.

(10) The interlabial pad according to any one from (7) to (9), wherein the mini-sheet piece is composed of a water-permeable sheet, a water-impermeable sheet, or a member formed by laminating the water-permeable sheet and the water-impermeable sheet.

In the interlabial pad with the flap portions according to the present invention, the mini-sheet piece attached thereto is composed of a water-permeable sheet or a water-impermeable sheet or a laminate formed by laminating both.

Here, if the mini-sheet piece forms the finger insertion opening, the mini-sheet piece is relaxed towards the opposite direction from the body side after fixing the interlabial pad and pulling out the finger from the finger insertion opening. So, when removing the used interlabial pad, the wearer can pull the mini-sheet piece. However, if the mini-sheet piece is entirely or partially composed of the water-impermeable material, when the wearer grasps the mini-sheet piece, the fingers will not be soiled so as to realize hygienic handling.

(11) The interlabial pad according to any one from (1) to (10), wherein the adhesive portion provided on the flap portion has a separation strength of 0.3 to 2.0 N and a shear strength of 0.5 to 15.0 N.

In the interlabial pad with the flap portions according to the present invention, the adhesion strength of total adhesive area provided on the pair of flap portions is strong enough not to cause positional displacement of the interlabial pad when it is worm. The adhesion strength, however, does not cause excessive loads or pains to the wearer's skin when the flap portions are removed. Specifically, for measuring separation strength, the adhesive was put on a polyester film and pressed to adhere to the polyester film by a roller with load of 30 g/cm$^2$ on a stainless steel board. The separation strength measured at pulling speed of 100 mm/min and separating angle of 180° was from 0.3 to 2.0 N. For measuring the shear strength, the adhesive was put on a polyester film and pressed to adhere to the polyester film by a roller with load of 30 g/cm$^2$ on a stainless steel board. The shear strength measured by pulling horizontally at pulling speed of 100 mm/min was 0.5 to 15.0 N. So, the wearer does not have to be anxious about positional displacement when the pad is worn. The wearer does not suffer from unpleasantness or pains when the pad is removed. The wearer can use the interlabial pad having superb functionality.

(12) The interlabial pad according to any one from (1) to (11), comprising a long convex area extending in the longitudinal direction of the body side face.

In the interlabial pad with the flap portions according to the present invention, the long convex area is provided towards the body side face in the longitudinal direction of the body side face of the interlabial pad. So, when the wearer fixes the interlabial pad with the flap portions, the long convex area enters near the ostium vaginae in between the labia minora at further depth of the interlabial space so as to reduce significantly the gap created between the interlabial pad and the labia.

Here, if the long convex area is formed by folding the interlabial pad (see FIG. 11), the long convex area can be readily deformed according to the anatomical topography of the wearer's labia by the pressure applied when the interlabial pad is worn. So, being different from the case that a ready-made convex portion provided on the body side face of the interlabial pad, the incident that the convex area does not fit between the wearer's labia due to individual differences may not occur. It is possible to fit the long convex area into the interlabial space irrespective of individual differences in the labia shape.

In the case that the long convex area is formed by folding the interlabial pad as shown above and that the mini-sheet piece is attached to the opposite side face to the body side face, the mini-sheet piece has a function to form the finger insertion opening as well as to restrict the enlargement of the inflection area in the main body of the interlabial pad so as to prevent the long convex area from being transformed.

(13) The interlabial pad according to any one from (1) to (12), wherein the interlabial pad is used together with a sanitary napkin.

The interlabial pad with the flap portions according to the present invention can be used with a sanitary napkin. So, even if the interlabial pad absorbs body fluid whose quantity exceeds the allowable level, it is surely possible to prevent body fluid from leaking and soiling the undergarments.

Further, if a sanitary napkin overlaps another sanitary napkin, there is possibility that unpleasant bulky feeling is generated, and that sanitary napkins become conspicuous, and that rash and excessive humidity take place since sanitary napkins are layered in unneeded area. On the other hand, using the interlabial pad of the present invention can prevent these disadvantages as the sanitary napkin overlaps the interlabial pad only around the ostium vaginae. In addition, the wearer does not have to carry sanitary napkins whose size is conspicuous since it is possible to replace only the interlabial pad with the flap portions according to the present invention while the sanitary napkin is not changed.

(14) The interlabial pad according to any one from (1) to (13), wherein the interlabial pad can be used as an incontinence pad.

The interlabial pad according to the present invention can be used also as an incontinence absorption pad. More specifically, since the ostium vaginae that discharges menstrual blood and the urethral meatus that discharges urine are positioned between the labia, if the interlabial pad according to the present invention is pinched in the interlabial space to be used, it can absorb urine.

Thus, according to the present invention, the urine can be absorbed at the interlabial space, especially near the urethral meatus, providing an effective absorptive pad for incontinence, in particular, for mild incontinence.

(15) The interlabial pad according to any one from (1) to (13), wherein the interlabial pad can be used as a vaginal discharge absorption pad.

The interlabial pad according to the present invention can be used also as a vaginal discharge absorption pad. More specifically, if the interlabial pad according to the present invention is pinched in the interlabial space to be used, it can absorb secretions (vaginal discharge) other than menstrual blood. So, it can be used for that purpose (for absorbing vaginal discharge).

Thus, the interlabial pad according to the present invention is also effective for the wearer who is not menstruating since it can relieve the wearers from uncomfortable feeling by absorbing vaginal discharge.

(16) A wrapping body composed of the interlabial pad according to any one from (1) to (15) and a wrapping container that contains the interlabial pad, wherein the flap portions provided on the interlabial pad is temporarily fixed detachably to an inner face of the wrapping container.

In the wrapping body according to the present invention, the flap portion provided on the interlabial pad is temporarily fixed directly to the inner face of the wrapping container. In other words, the wrapping container is formed in such a way that the region to be temporarily fixed to the flap portions of the interlabial pad constitutes a part of the wrapping container. Specifically, the flap portions can be temporarily fixed by applying separation treatment with silicon, fluorocarbon resins, etc. to either whole inside area or only the area to which the flap portions are temporarily fixed in the inner face of the wrapping container, or coating the area to which the flap portions are temporarily fixed with separate sheets applied with separation treatment with silicon, fluorocarbon resins, etc. When separable sheets are attached, the non-separation face of the separable sheets is bonded to the wrapping container through an adhesive.

As shown above, in the present invention, the portion having separation function is integrated with the wrapping container. So, it is not required to remove an separation paper attached to the flap portion in addition to unwrapping the wrapping container as in the case that a separation paper is separately attached to the flap portion so that the interlabial pad may be take out smoothly. In addition, since a disposing process to trash wastes may be saved, it becomes easier to wear the pad. Further, since the pair of flap portions to which an adhesive is applied are prevented from being bonded with each other, it is easier to retrieve and fit the pad.

(17) A wrapping body composed of the interlabial pad recited in (7) or (9) and a wrapping container that wraps the interlabial pad, wherein the flap portions provided on the interlabial pad are temporarily fixed detachably to an inner face of the wrapping container, and wherein the interlabial pad is folded and contained such that the finger insertion opening opens when the wrapping container is unsealed.

In the wrapping body according to the present invention, the interlabial pad with the flap portions is contained in the wrapping container in such a way that the finger insertion opening provided on the interlabial pad is opened. So, the wearer can insert her finger into the finger insertion opening soon after unsealing the wrapping container to hold the interlabial pad with the flap portions at the fingertip.

In this respect, with regard to a sheet shaped sanitary product such as a sanitary napkin, contents thereof are generally folded for compact wrapping. In addition to the compact wrapping described above, the present invention has a function that the folded interlabial pad is unfolded when the individual wrapping container for the interlabial pad is unsealed so that a gap is generated between the mini-sheet piece and the back side sheet of the interlabial pad to form the finger insertion opening automatically.

This kind of folding method include, for example, folding the interlabial pad along the substantially longitudinal centerline in such a way that the side of the interlabial pad having the mini-sheet piece faces inward.

(18) The wrapping body according to (16) or (17), wherein the wrapping container comprises a series of wrapping sheets rolled so as to form an overlapped region which is overlapped by itself in a portion of the series of wrapping sheets, wherein the inner face to which the flap portions are temporarily fixed comprises an inner portion of a face having both side edges to form the overlapped portion.

In the wrapping body according to the present invention, the flap portions provided on the interlabial pad are folded integrally with the wrapping sheet. So, the interlabial pad is contained in a compact fashion though the area of the interlabial pad is increased because of the flap portions. Thus, the wearer can use the interlabial pad with higher functionality while maintaining the same portability as the interlabial pad without the flap portions.

BEST MODE OF THE CARRYING OUT THE INVENTION

The interlabial pad with the flap portions of the present invention will now be explained more specifically by referring to the following figures.

[First Embodiment]

<Structure of the Interlabial Pad with the Flap Portions>

Figure 1:
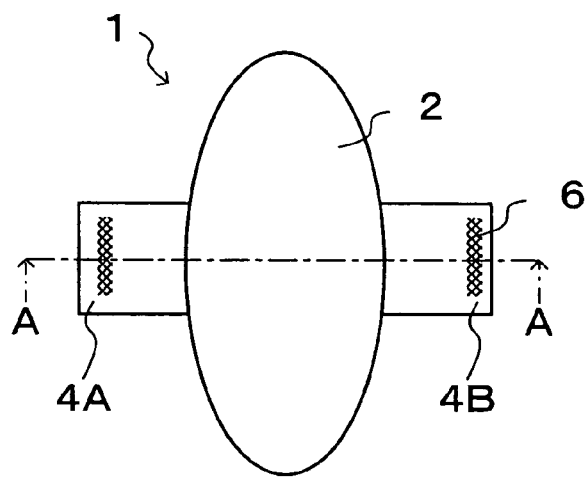
FIG. 1 is a schematic perspective view showing the body side face of the interlabial pad with the flap portions according to the first embodiment.
Figure 2:
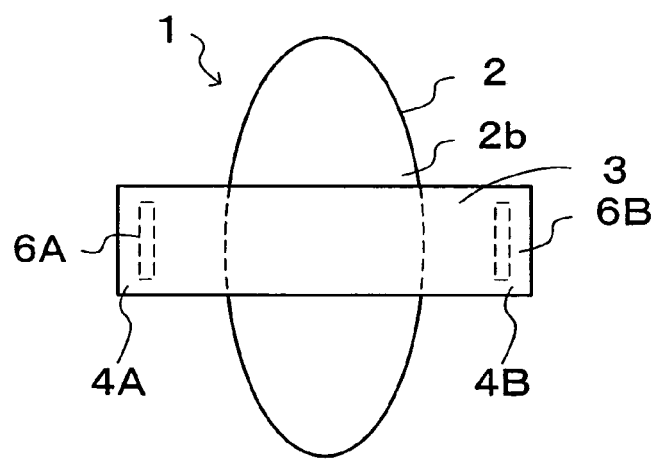
FIG. 2 is a schematic perspective view showing the opposite side face to the body side face of the interlabial pad with the flap portions according to the first embodiment.
Figure 3:
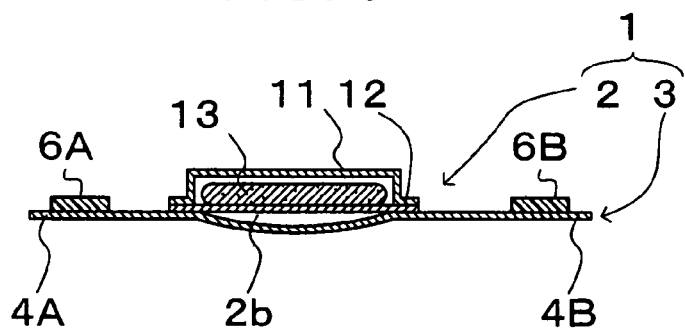
FIG. 3 is a cross section A—A in FIG. 1.
Figure 4:
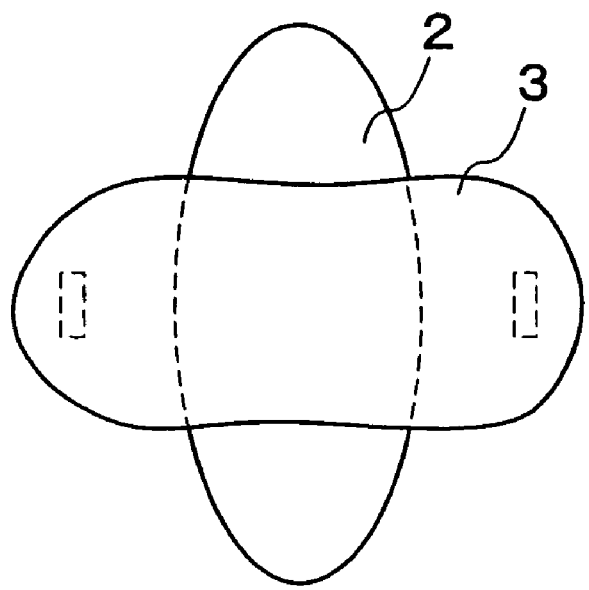
FIGS. 4A–B illustrate another configuration of the interlabial pad with the flap portions of the first embodiment.
Figure 4:
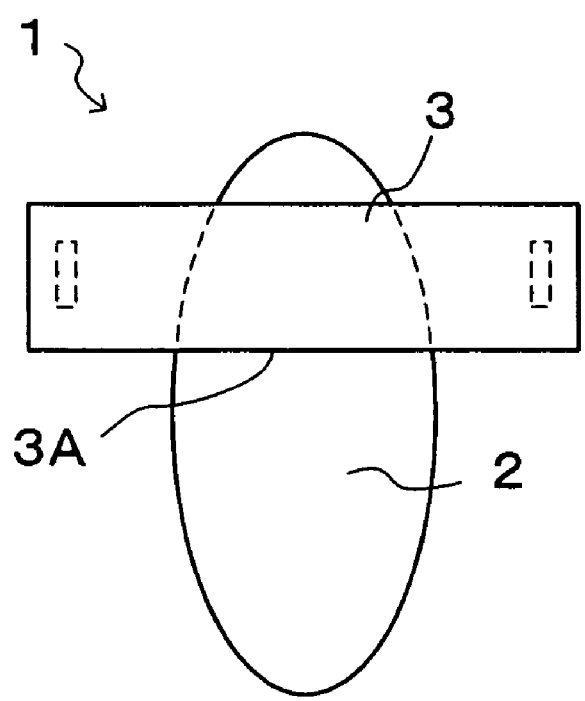

FIG. 1 is a simplified perspective view showing the body side face of the interlabial pad with of the flap portions according to the first embodiment. FIG. 2 is a simplified perspective view showing the opposite side to the body side of the interlabial pad with of the flap portions according to the first embodiment. FIG. 3 is a cross section A—A in FIG. 1. FIG. 4 is a view showing another configuration of the interlabial pad with the flap portions.

As shown in FIG. 1, the interlabial pad 2 has the lateral dimension and the longitudinal dimension, the latter being substantially longer than the former. And as shown in FIG. 2, the mini-sheet piece 3 having a lateral dimension that is larger than that of the interlabial pad 2 is attached to the opposite side face to the body side face 2b of the interlabial pad 2 in such a way that a part of the mini-sheet piece 3 protrudes from the both side edges of the interlabial pad 2 with heat seal or an adhesive. The protruded regions constitute the flap portions 4A and 4B. The adhesive 6A and 6B are applied to the body side faces of the flap portions 4A and 4B respectively.

As shown in FIG. 3, the interlabial pad with the flap portions 1 of this embodiment comprises the water-permeable surface side sheet 11, the water-impermeable the back side sheet 12, the absorbent body 13 sandwiched between the surface side sheet 11 and the back side sheet 12, the interlabial pad 2 constituted of the water-permeable surface side sheet 11 and the water-impermeable the back side sheet 12 bonded at the peripheral part of the absorbent body 13 and the mini-sheet piece 3 attached to the opposite side face to the body side face 2b of the interlabial pad 2.

Furthermore, in this embodiment, the mini-sheet piece 3 is rectangular. However, for example, as shown in FIG. 4(A), it may be oblong shaped by cutting the sides roundly. As shown above, making the side of the flap round reduces the pricking sensation of skin due to the side of the flap portion is reduced.

Also in this embodiment, the mini-sheet piece 3 is attached to the central part of the interlabial pad 2. However, as shown in FIG. 4(B), the mini-sheet piece 3 can be attached to the region near the ends of interlabial pad 2. If the mini-sheet piece 3 is attached to such a position, it is possible to prevent the fingertip inserted into the finger insertion opening 3A from being exposed too much and menstrual blood from soiling the fingertip when fixing the interlabial pad 1.

<Attachment of the Interlabial Pad with the Flap Portions>

The procedure to fix the interlabial pad with the flap portions 1 of this embodiment will now be explained.

Figure 5:
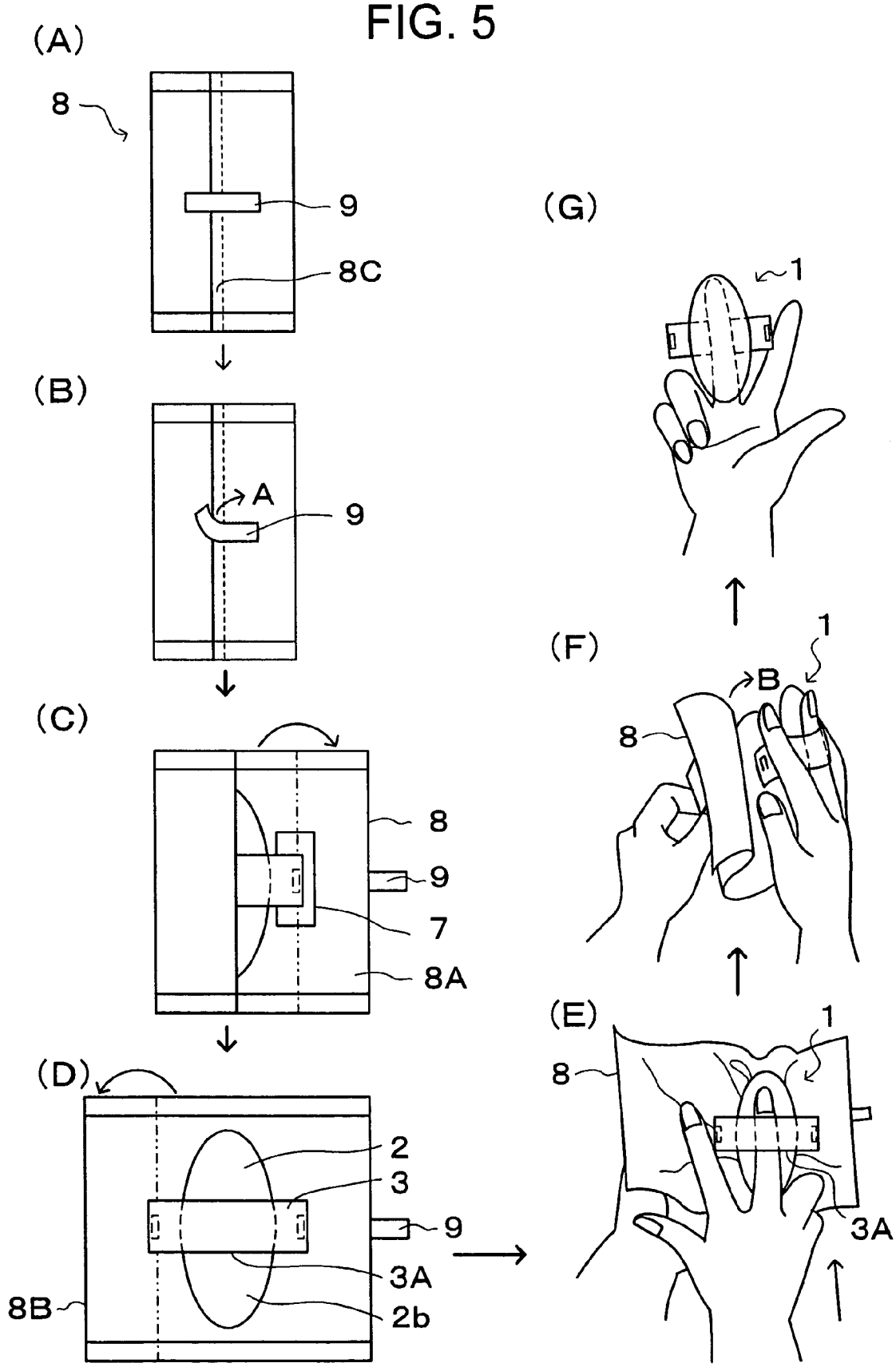
FIGS. 5A–G illustrate a process chart of the procedure from unsealing the wrapping container to attaching the interlabial pad with the flap portions of the first embodiment to the fingertip.
Figure 6:
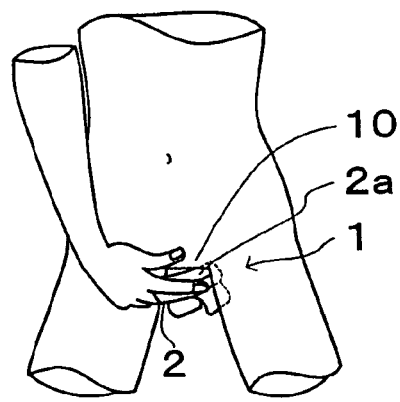
FIGS. 6A–E illustrate a process chart of the procedure to hold the interlabial pad of the first embodiment with the flap portions at the fingertip and to fit it to the interlabial space.
Figure 6:
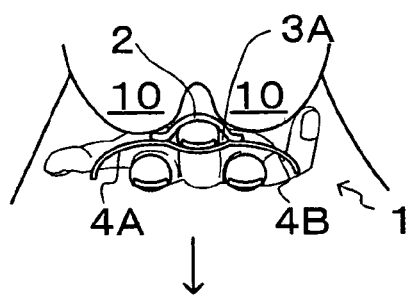
Figure 6:
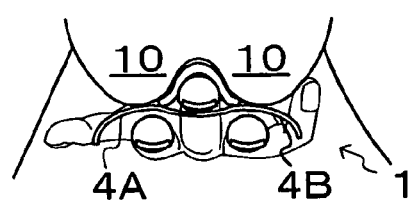
Figure 6:
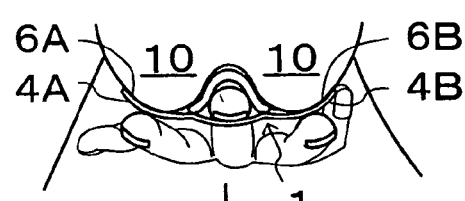
Figure 6:
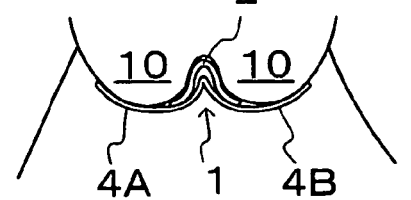

FIG. 5 is a process chart of the procedure from unsealing the wrapping container to attaching the interlabial pad with the flap portions 1 to the fingertip. FIG. 6 is a process chart of the procedure to fix the interlabial pad with the flap portions 1 held at the fingertip to the interlabial space 10.

As shown in FIG. 5(A), the fixing tape 9 is affixed to the overlapped portion 8C of both side edges of the wrapping sheet 8 constituting the wrapping container to contain the interlabial pad with the flap portions 1. So, the wearer, as shown in FIG. 5(B), can open the one side 8A of the wrapping sheet 8 outwardly by pinching and pulling the fixing tape 9 in "A" direction as shown in FIG. 5(C).

Then, as shown in FIG. 5(D), the mini-sheet piece 3 attached to the interlabial pad 2 is exposed by also opening other side 8B outwardly. Thus, the wearer can find the finger insertion opening 3A formed between the mini-sheet piece 3 and the opposite side face to the body side face 2b of the interlabial pad 2 and as shown in FIG. 5(E), can immediately insert her finger of the dominant hand (normally right hand) into the finger insertion opening 3A. And, as shown in FIG. 5(F), the interlabial pad with the flap portions 1 can be retrieved from the wrapping sheet 8 by grasping the wrapping sheet 8 by the left hand, and raising the right hand towards B direction. As a result, as shown in FIG. 5(G), the interlabial pad with the flap portions 1 can be retrieved from the wrapping container with the interlabial pad 1 held at the tip of the long finger of the left hand.

In order to fix the interlabial pad with the flap portions 1 retrieved as shown above to the labia, first, as shown in FIG. 6(A) seen from the front side of the wearer, the body side face 2a of the interlabial pad 2 is made fitted to the labia 10. Then, as shown in FIG. 6(B) seen from the rear side of the wearer, the long finger inserted into the finger insertion opening 3A is put between the labia 10 through the interlabial pad 2. Then, as shown in FIG. 6(C), the interlabial pad 2 is made to enter the labia 10 by pushing and opening the labia 10. Then, as shown in FIG. 6(D), the flap portions 4A and the flap portions 4B is positioned according to the shape of the labia 10 with the forefinger and the annular finger respectively. Then, the flap portions 4A and 4B are made to stick to the surface of the labia 10 with the adhesive 6A and 6B respectively and the long finger is pulled out from the finger insertion opening 3A. By this procedure, as shown in FIG. 6(E), the inner side in the interlabial pad 2 is fitted to the inner surface of the labia 10 and the flap portions 4A and 4B are fixed to the outer side of the labia 10. Even if a large quantity of body fluid is discharged, it is possible to prevent the interlabial pad 2 from being displaced.

<Wrapping Method of the Interlabial Pad with the Flap Portions>

Figure 7:
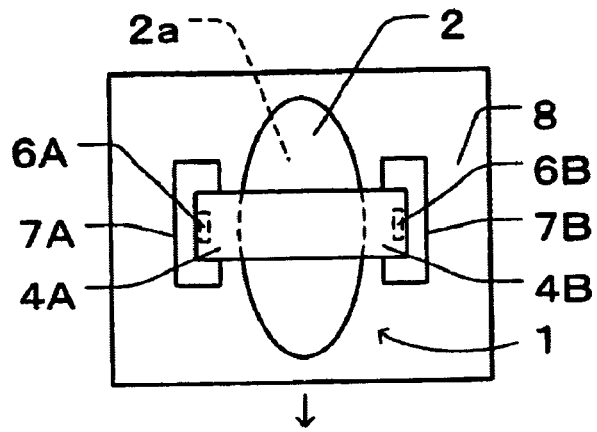
FIGS. 7A–D illustrate a process chart of the procedure to wrap the interlabial pad of the first embodiment in a wrapping sheet to make a wrapping body.
Figure 7:
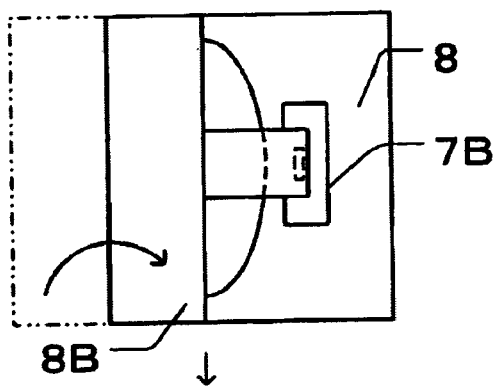
Figure 7:
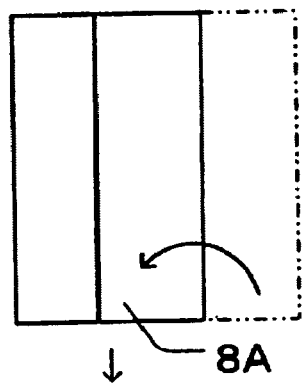
Figure 7:
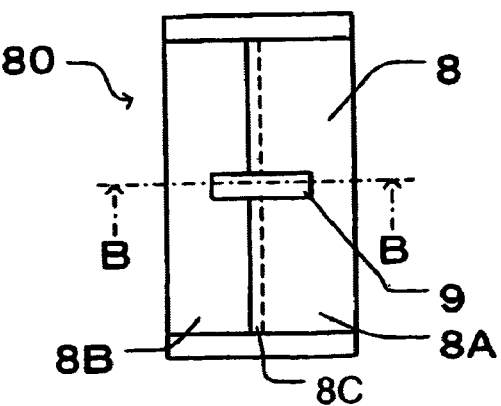
Figure 8:
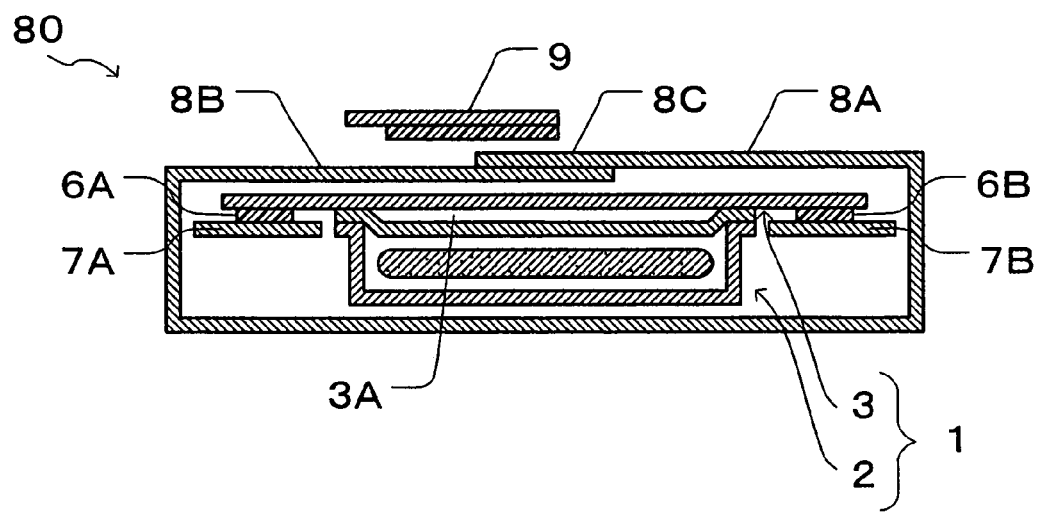
FIG. 8 is a cross section B—B of the wrapping body in FIG. 7(D).

The procedure to wrap the interlabial pad with the flap portions 1 in the wrapping sheet 8 to form the wrapping body 80 will now be explained. FIG. 7 is a process chart showing the process to cover the interlabial pad with the flap portions 1 in the wrapping sheet 8 to form the wrapping body 80. FIG. 8 is a cross section of B—B in FIG. 7(D).

As shown in FIG. 7(A), the interlabial pad with the flap portions 1 is arranged in such a way that the body side face 2a of the interlabial pad 2 contacts the wrapping sheet 8. In this case, the separate sheets 7A and 7B are affixed on the positions where the adhesive 6A and 6B that are applied on the flap portions 4A and 4B are positioned. By this, the flap portions 4A and 4B are detachably attached to the wrapping sheet 8. And as shown in FIG. 7(B), one side 8B of the wrapping sheet 8 is folded inwardly, and as shown in FIG. 7(C), the other side 8A is folded inwardly. Then, as shown in FIG. 7(D), the overlapped portion 8C formed by the side 8A and 8B, and the front and rear end of the wrapping body 80 are re-separatably sealed respectively the fixing tape 9 is affixed to maintain the sealed state to form the wrapping body 80.

As shown in FIG. 8, the interlabial pad with the flap portions 1 is so arranged that the mini-sheet piece 3 is positioned just below the overlapped region 8C where one side 8A and the other the side 8B of the wrapping sheet 8. So, the wearer can find the mini-sheet piece 3 and insert her finger into the finger insertion opening 3A formed between the interlabial pad 2 and the mini-sheet piece 3 immediately after unsealing the overlapped portion 8C by pulling the fixing tape 9.

[Second Embodiment]

<Structure of the Interlabial Pad with the Flap Portions>

The interlabial pad with the flap portions of the second embodiment will now be explained.

Figure 9:
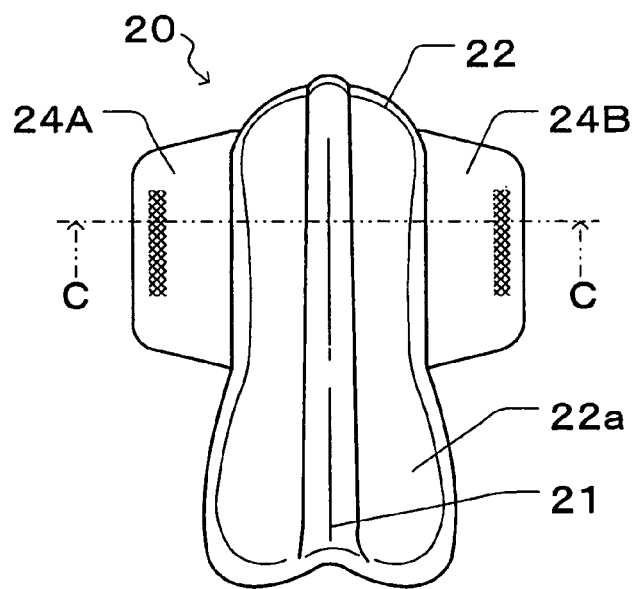
FIG. 9 is a view showing the body side face of the interlabial pad with the flap portions of the second embodiment.
Figure 10:
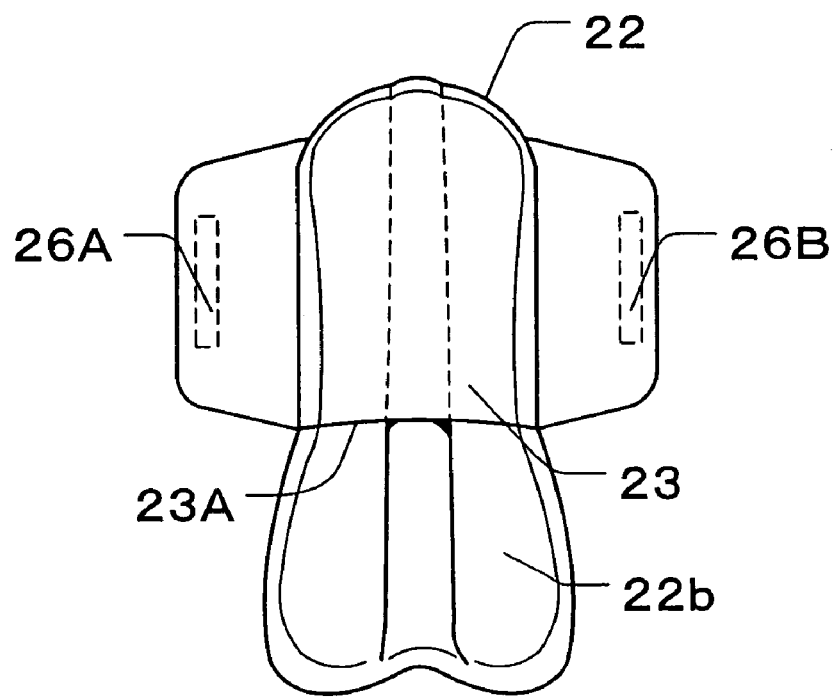
FIG. 10 is a view showing the opposite side face to the body side face of the interlabial pad with the flap portions of the second embodiment.
Figure 11:
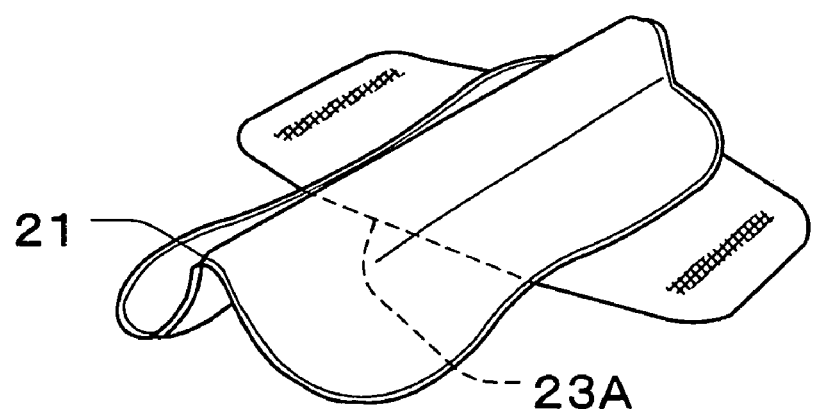
FIG. 11 is a perspective view of the interlabial pad with the flap portions of the second embodiment.
Figure 12:
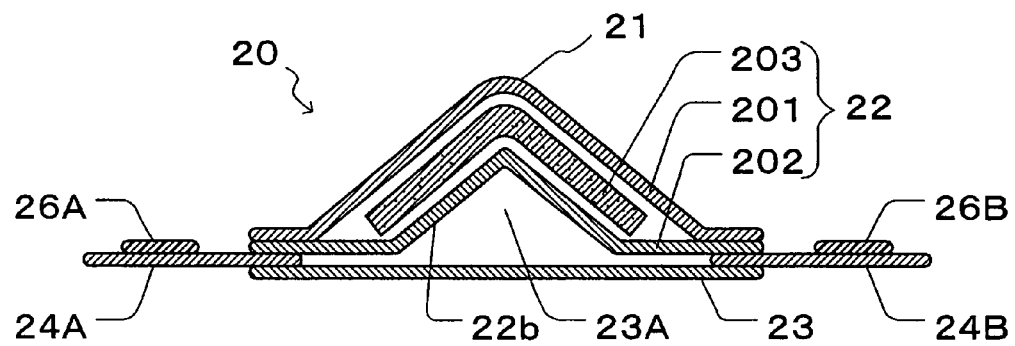
FIG. 12 is a cross section C—C of FIG. 9 showing the inner structure of the interlabial pad with the flap portions of the second embodiment.

FIG. 9 is a view showing the body side face of the interlabial pad with the flap portions 20 of the second embodiment. FIG. 10 is a view showing the opposite side face to the body side face of the interlabial pad with the flap portions 20. FIG. 11 is a perspective view of the interlabial pad with the flap portions 20. FIG. 12 is a cross section C—C of FIG. 9.

As shown in FIG. 9, the interlabial pad with the flap portions 20 of this embodiment comprises the interlabial pad 22, the flap portions 24A and 24B at both sides of the interlabial pad 22 and the long convex area 21 on the body side face 22a of the interlabial pad 22. In addition, as shown in FIG. 10, the interlabial pad with the flap portions 20 of this embodiment also comprises the mini-sheet piece 23 on the opposite side face to the body side face 22b of the interlabial pad 22. The finger insertion opening 23A is formed between the mini-sheet piece 23 and the opposite side face to the body side face 22b of the interlabial pad 22. So, as shown in FIG. 11, it is possible to smoothly insert a finger into the finger insertion opening 23A from the gap formed at the inner side of the long convex area 21.

As shown in FIG. 12, the interlabial pad with the flap portions 20 of this embodiment is constituted of the interlabial pad 22 having a laminate structure where the absorbent body 203 is sandwiched between the water-permeable surface side sheet 201 and the water-impermeable back side sheet 202, the surface side sheet 201 and the back side sheet 202 are bonded to each other at the peripheral part of the absorbent body 203, the flap portions 24A and 24B attached to the opposite side face to the body side face 22b of the interlabial pad and the mini-sheet piece 23 attached to the position where the interlabial pad 22, the flap portions 24A and 24B are bonded to one another.

The interlabial pad 22 is folded in such a way that it convexes towards the body side face. The long convex area 21 is formed at the folded region. The finger insertion opening 23A is formed between the long convex area 21 and the mini-sheet piece 23. The adhesive 26A and 26B are applied to the skin-touching surface of the flap portions 24A and 24B.

<Attachment of the Interlabial Pad with the Flap Portions>

Figure 13:
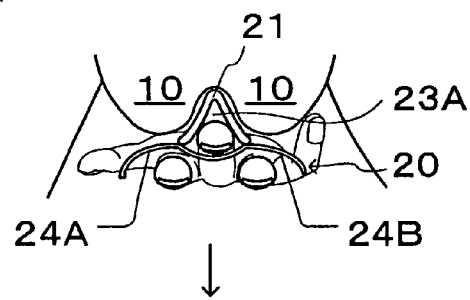
FIGS. 13A–B illustrate a process chart of the procedure to fit the interlabial pad with the flap portions of the second embodiment to the labia.
Figure 13:
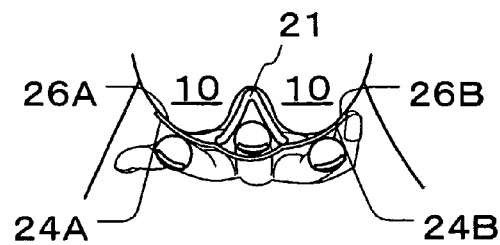

Attachment state of the interlabial pad with the flap portions 20 according to this embodiment will now be explained. FIG. 13 is a process chart showing the procedure to fix the interlabial pad 20 with the flap portions to the labia 10.

Figure 14:
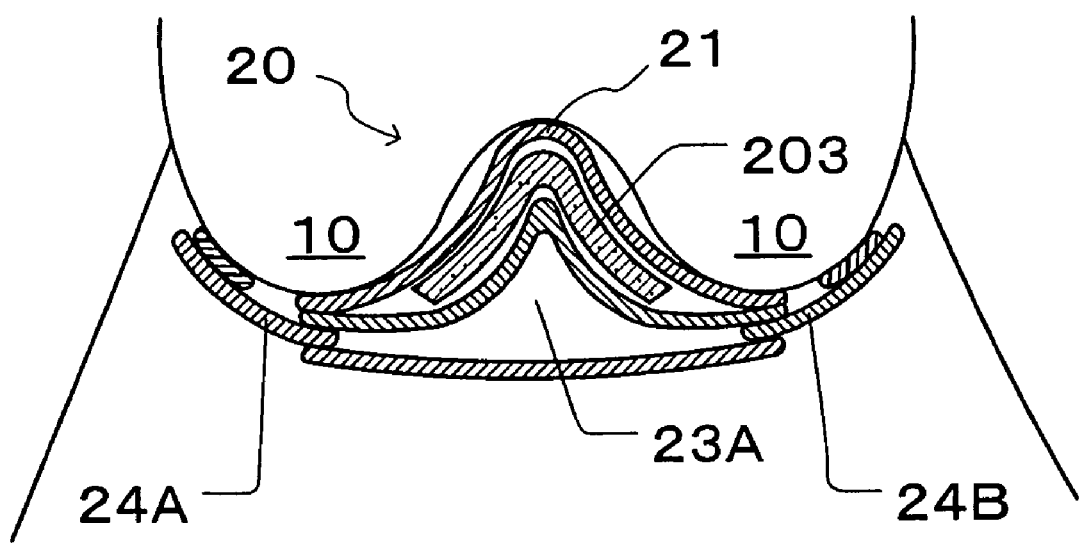
FIG. 14 is a cross section view showing the state that the interlabial pad with the flap portions of the second embodiment is fitted to the labia.

FIG. 14 is a longitudinal sectional view showing the state the interlabial pad with the flap portions 20 is fit to the labia 10.

As shown in FIG. 13(A), the long finger is inserted into the finger insertion opening 23A and the long convex area 21 is fit to the labia 10 in order to fix the interlabial pad with the flap portions 20.

Then, as shown in FIG. 13(B), the flap portions 24A and the flap portions 24B are positioned on the surface of the labia 10 by the forefinger and the annular finger and sticked onto the surface with the adhesive 26A and 26B respectively. Thus, as shown in FIG. 14, the interlabial pad 20 is fixed while the long convex area 21 containing the absorbent body 203 is fit in the back of the labia 10. So, menstrual blood discharged from the ostium vaginae is surely absorbed by the long convex area 21 preventing menstrual blood from leaking.

[Flap Portion]

The flap portions of the interlabial pad with the flap portions according to the present invention will now be explained.

Any structures and shapes are usable for the flap portion so long as they are exposed outside of the interlabial space and can be arranged to cover the labia majora when the interlabial pad is fitted to the interlabial space.

Figure 15:
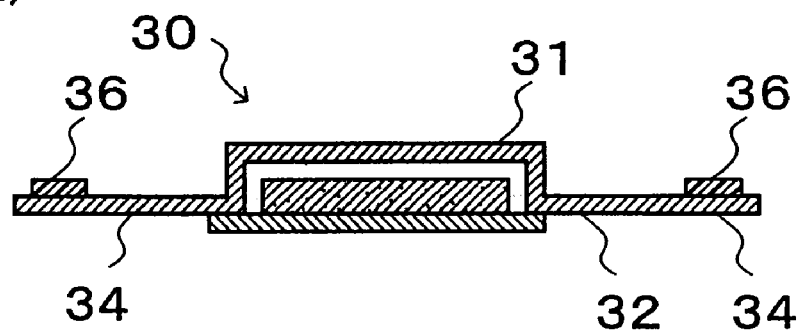
FIGS. 15A–C illustrate a cross section view showing the state that the flap portion is constituted of a part of the interlabial pad.
Figure 15:
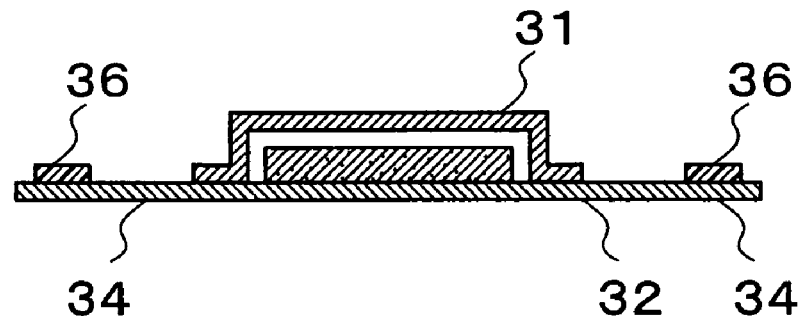
Figure 15:
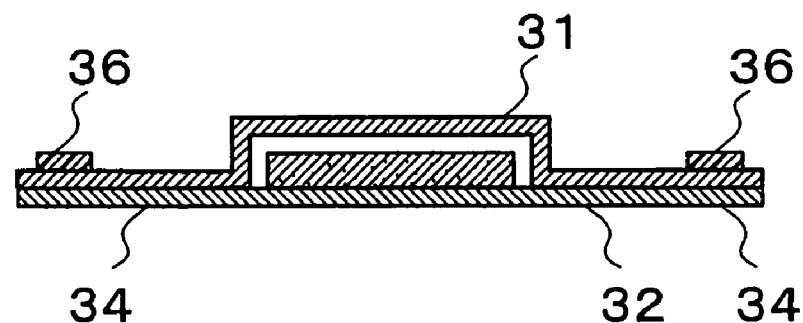

For example, as the interlabial pad with the flap portions 1 and 20 according to the first and the second embodiment shown above, the flap portions may be formed of a sheet independent of the interlabial pad bonded to the side edges of the interlabial pad. Further, for example, the flap portion 34 may be formed any one of the protruded surface side sheet 31 of the interlabial pad 30 as shown in FIG. 15(A), the protruded back side sheet 32 as shown in FIG. 15(B), or the surface side sheet 31 and the back side sheet 32 of the interlabial pad 30 respectively protruded by the same area as shown in FIG. 15(C).

Figure 16:
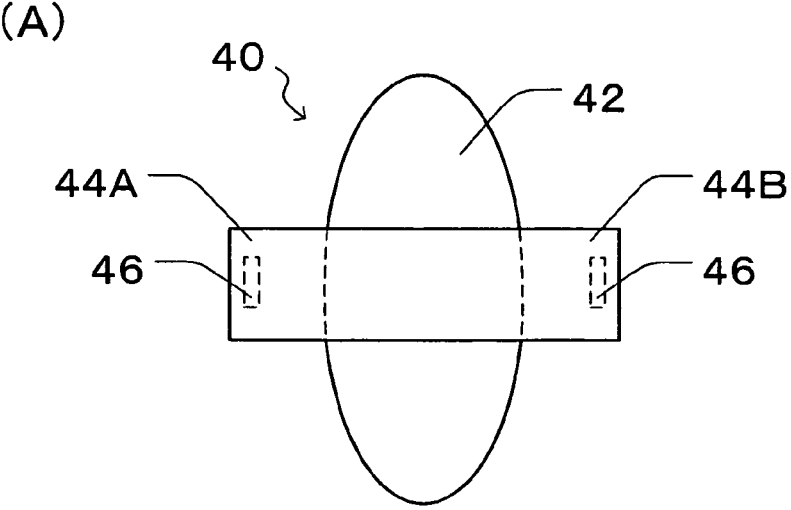
FIGS. 16A–C illustrate a view showing other configurations of the flap portions.
Figure 16:
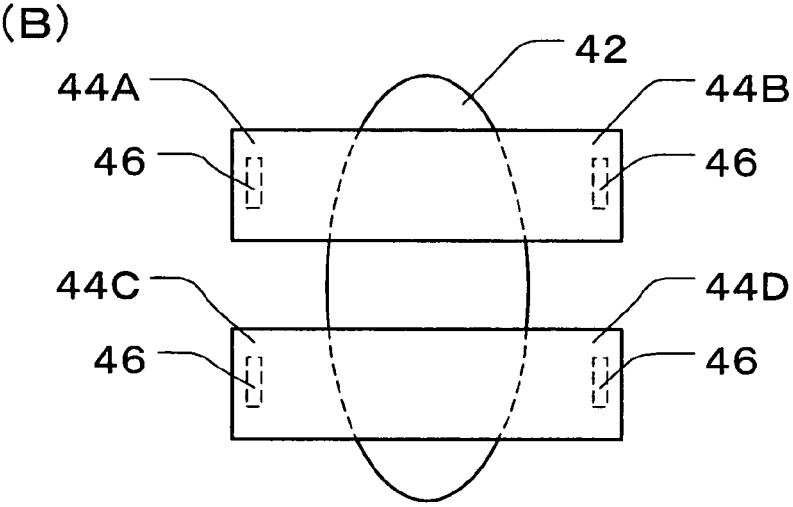
Figure 16:
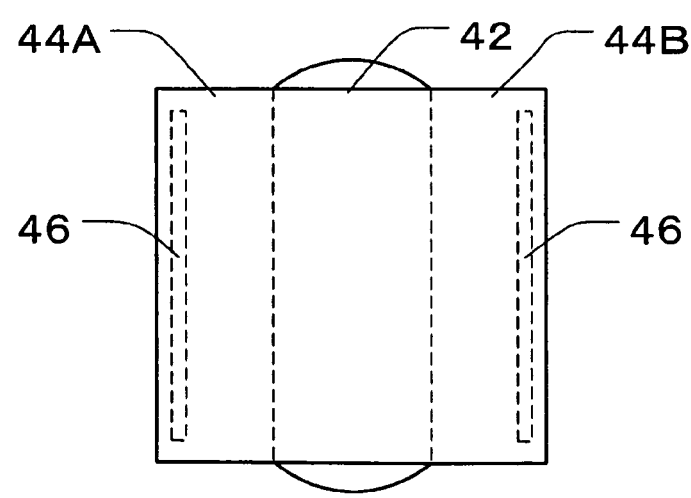

The flap portions may be provided, as shown in FIG. 16(A), in such a manner that the flap portion 44A is provided at one side and 44B the other, symmetrically in the middle area of the interlabial pad 42, or 44A and 44C at one side, and 44B and 44D are at the other, multiple flaps being provided at each side as shown in FIG. 16(B). Or, the flap portions 44A and 44B may be provided entirely along each side edge as shown in FIG. 16(C). As shown above, it is possible to change the strength to fix the interlabial pad against the labia by changing the shape of the flap portions accordingly. In addition, the adhesive 46 is applied to each flap portion. The application area will change depending on the size of the flap portions.

[Interlabial Pad]

The interlabial pad will now be explained. In the interlabial pad 2 of the first embodiment and the interlabial pad 22 of the second embodiment, the absorbent body is contained between the surface side sheet and the back side sheet bonded to each other at their margins. However, it should be understood that the interlabial pad is not limited to the specific embodiments described in the specification. It may be an enclosure structure where a water-impermeable sheet is provided under the absorbent body, they are enclosed by a water-permeable cover sheet and the margin is bonded so that the absorbent body is not removed.

With regard to constructing the interlabial pad, for example, for bonding the surface side sheet and the absorbent body, the absorbent body and the back side sheet, and the surface side sheet and the back side sheet, etc., adhesives may be selected from the groups of pressure-sensitive adhesives composed mainly of water-insoluble synthetic rubbers such as styrene-ethylene-butadiene-styrene block copolymers (SEBS), styrene-butadiene-styrene block copolymers (SBS), styrene-isoprene-styrene block copolymers (SIS), etc.; thermo sensitive adhesives mainly composed of synthetic rubbers such as ethylene-vinyl acetate copolymers (EVA); adhesives or starch glue composed mainly of water-soluble thermoplastic polyvinyl alcohol (PVA); water-sensitive gels composed mainly of an acrylic acid, containing a crosslinking agent and a plasticizer or water; water-insensitive gel composed mainly of a silicon, containing a crosslinking agent and a plasticizer, etc. Further, adhesive application patterns include planate pattern, stripe pattern, dot pattern, spiral pattern, etc.

[Other Structures of the Interlabial Pad]

Figure 17:
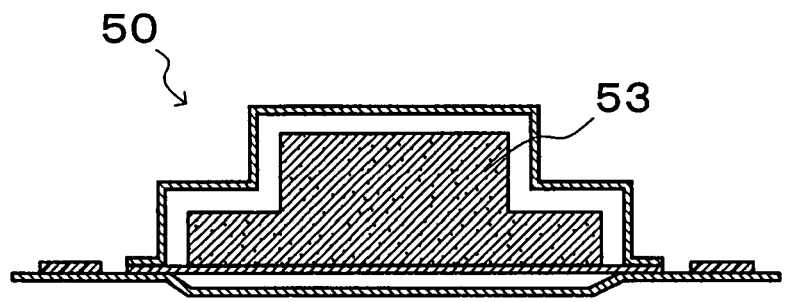
FIG. 17 is a view showing the interlabial pad containing an absorbent body with convex structure where the middle region is raised.
Figure 18:
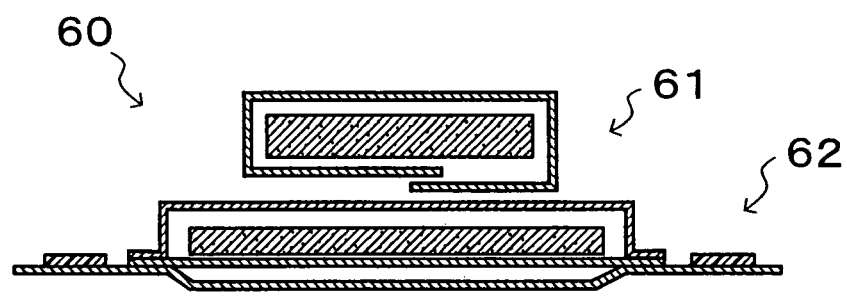
FIG. 18 is a view showing an interlabial pad composed of two sheets having different length dimension in the lateral direction.
Figure 19:
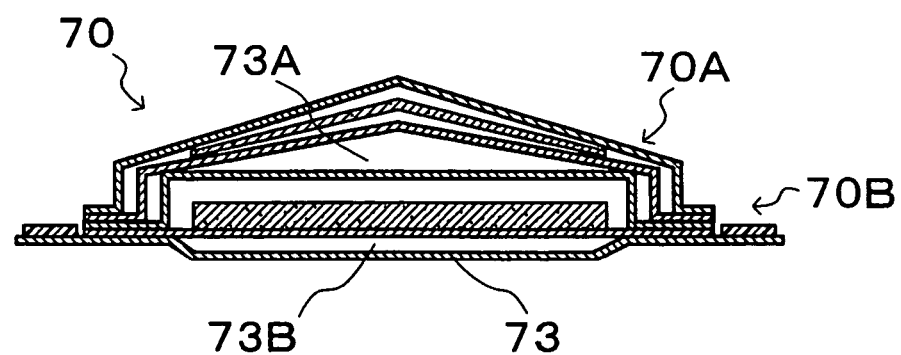
FIG. 19 is a view showing an interlabial pad constituted of two layers; the main sheet body and the sub sheet body.

Other structures of the interlabial pad will now be explained. FIG. 17 is a view showing the interlabial pad 50 containing an absorbent body with convex structure where the middle region is raised. FIG. 18 is a view showing an interlabial pad 60 composed of two sheets having different length dimension in the lateral direction. FIG. 19 is a view showing an interlabial pad 70 constituted of the two layers; the main sheet body 70A and the sub sheet body 70B.

In the interlabial pad 50 shown in FIG. 17, the absorbent body 53 contained is partly raised in the center of the lateral axis in order to improve the fit between the wearer's interlabial space and the interlabial pad 50 preventing menstrual blood from leaking outward.

In the interlabial pad 60 shown in FIG. 18, the auxiliary sheet body 61 having smaller length in the lateral direction is overlaid on the body side face of the ordinal interlabial pad 62, they are bonded to each other at the front and rear side with an adhesive, heat seal, ultrasonic seal, etc.; the overlapped regions are bonded with an adhesive, or bonded with combination thereof.

As shown above, attaching the auxiliary sheet body 61 improves body fluid absorbing function and menstrual blood leakage prevention function of the interlabial pad 62.

In addition, the interlabial pad 70 shown in FIG. 19 comprises the main sheet body 70A and the sub sheet body 70B. Both of them are in bonded state at each side in the longitudinal direction. Inside of them, they stay away from each other and at least one sleeve portion of the both sleeve portion is in non-bonded state in the lateral direction. So, the wearer can insert her finger into two regions; the first finger insertion opening 73A between the main sheet body 70A and the sub sheet body 70B, the second finger insertion opening 73B between the mini sheet body 73 for the interlabial pad and the sub sheet body 70B. By this structure, the wearer can select either one of the finger insertion opening depending on the depth of her labia.

[Interlabial Pad with the Flap Portions used with the Sanitary Napkin]

Figure 20:
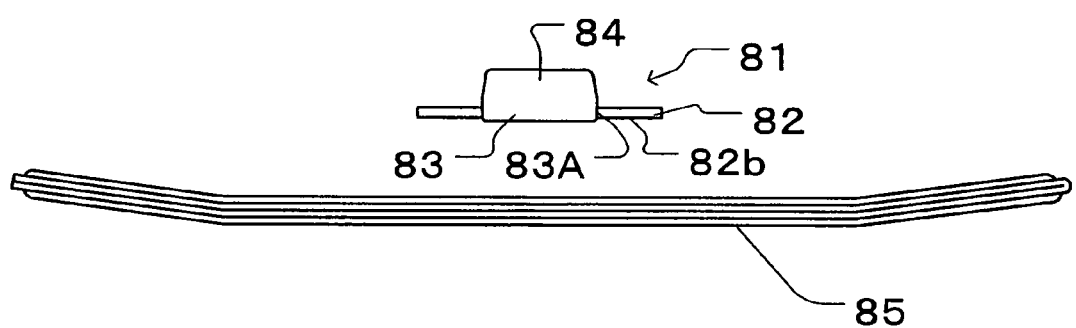
FIGS. 20A–B illustrate a view showing the state that the interlabial pad with the flap portions is used with a sanitary napkin.
Figure 20:
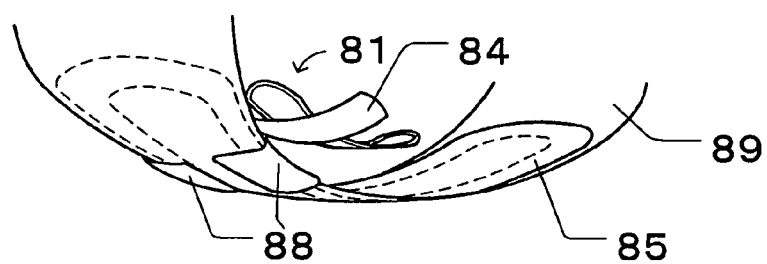

The interlabial pad with the flap portions used with the sanitary napkin will now be explained. FIG. 20 is a view showing the state the interlabial pad with the flap portions 81 for simultaneous use with the sanitary napkin and the sanitary napkin 85 are used at the same time.

As shown in FIG. 20(A), the interlabial pad with the flap portions 81 can be also used with the ordinary sanitary napkin 85. Thus, it is possible to use the interlabial pad with the flap portions 81 of the present invention more effectively even in the day when the quantity of discharge is large if used with the sanitary napkin 85. Furthermore, the fixing procedure of this kind of the interlabial pad with the flap portions 81 is as follows. That is, (i) unseal the wrapping container and expose the mini-sheet piece 83. (ii) Insert the finger into the finger insertion opening 83A in such a way that the finger cushion touches the opposite side face to the body side face 82b of the interlabial pad 82, hold the interlabial pad with the flap portions 81 at the fingertip. (iii) Fix the interlabial pad 82 along the vulvar cleft using finger pressure. (iv) Affix the adhesive 86 applied to the flap portions 84 to skin. (v) Fix the sanitary napkin 85 in the crotch portion of the undergarment. (vi) Pull up the undergarment to the specified position. Furthermore, the sanitary napkin 85 may be fixed to the undergarment before fixing the interlabial pad 82 to the labia.

The sanitary napkin may or may not have at least a pair of wings that are symmetrical. Furthermore, if it has a pair of wings, as shown in FIG. 20(B), the flap portions 84 of the interlabial pad 81 wraps the labia majora (now shown) situated above and while the wing 88 of the sanitary napkin 85 wraps the undergarment 89 situated below.

The size of the sanitary napkin usable for the sanitary napkin 85 is that can cover the external genitals of females. Specifically, the length is specifically 150 to 380 mm, more specifically selected from ranges; 150 to 225 mm, 225 to 270 mm or 270 to 380 mm depending on the wearer's experience, discharge quantity of menstrual blood, body type, behavior(situation of physical movement, sleep)etc. Thickness of the products usable herein include a thin type with thickness of 1 to 4 mm and a thick type with thickness of 5 mm or more.

The sanitary napkin used with the interlabial pad with the flap portions is provided with a water-permeable sheet on the skin contacting side, a water-impermeable sheet on a skin non-contacting side, the absorbent body between them and an adhesive applied to the water-impermeable sheet to fix to undergarments.

[Outer Dimension of the Interlabial Pad with the Flap Portions]

Outer dimension of the interlabial pad will now be explained.

Longitudinal and lateral dimension and dimension of the interlabial pad are selected from the range that the interlabial pad can be fitted to the interlabial space and retained by own gripping force considering the sealing property of the labia. Specifically, the longitudinal dimension is 60 to 150 mm, preferably 80 to 120 mm. Further, apparent length dimension of the interlabial pad in the lateral direction is preferably 10 to 60 mm, more preferably 20 to 40 mm. If the length dimension in the lateral direction is longer than 60 mm, since the area not pinched by the labia is rubbed by thighs of the wearer and the friction generated due to this exceeds the retaining force by both labia, the interlabial pad may be removed. On the contrary, if the length dimension in the lateral direction is smaller than 10 mm, since the area to be pinched between the labia becomes smaller, the area that lies in the interlabial space decreases and the contact area against the inner face of the labia is reduced to cause higher risk in removal of the interlabial pad.

Figure 26:
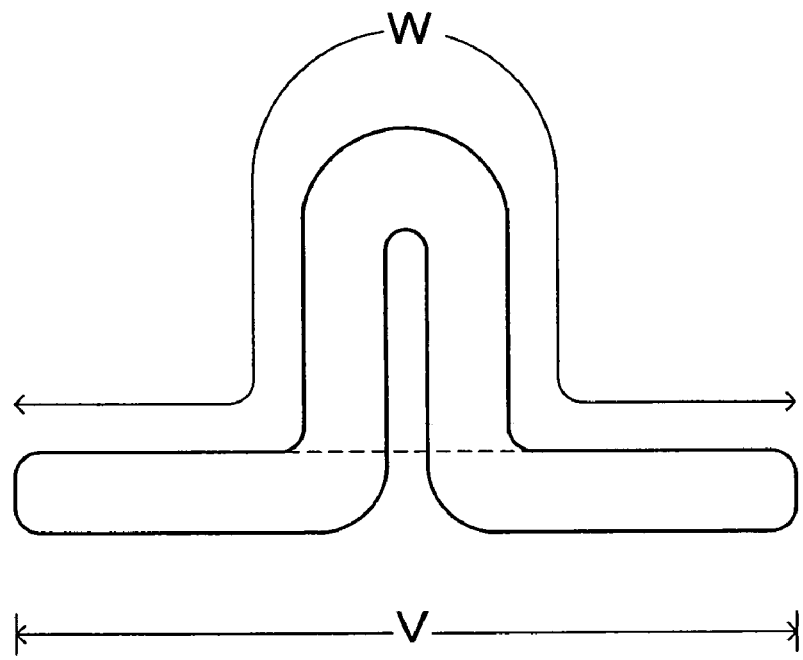
FIG. 26 is a schematic view showing the length dimension of the interlabial pad in the lateral direction.
Figure 27:
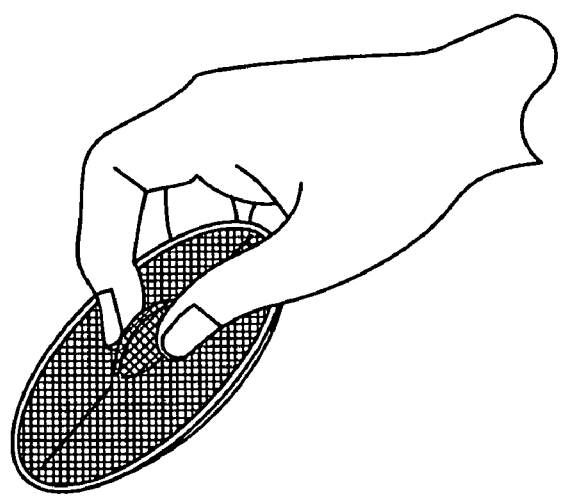
FIG. 27 is a view showing an example of a conventional interlabial pad.

As used herein, the term "apparent" refers to the distance between two points having the smallest length dimension (falls under V in FIG. 26). This is a deliberate definition considering the case where the distance between two points in plan extended from a three dimensional shape is sometimes used as an actual distance (falls under W in FIG. 26) in relation to manufacturing process.

The dimension of the absorbent body contained in the interlabial pad should be the same as or smaller than the interlabial pad leaving 2 to 10 mm from the margin of the interlabial pad considering the strength of the margin. The thickness of the absorbent body is 2 to 10 mm, preferably 3 to 6 mm in order to obtain amenity not to deteriorate wear feeling.

The length dimension in the longitudinal direction of the mini-sheet piece of the interlabial pad can be adjusted freely, not particularly limited. However, if the finger insertion opening is provided, it is desirable that a finger can be inserted into the finger insertion opening, the interlabial pad can be retained at the fingertip and insertion direction of the finger is pointed out. Specifically, it is at least at least 10 mm or more, preferably 10 to 40 mm considering operationality.

The dimension of one flap portion, specifically, the largest dimension of the basement as the side edge of the interlabial pad to the front edge of the flap portion is not particularly limited, however, should be at least 15 mm or more, preferably 15 to 50 mm if operationality is also considered. The area of the flap portion is preferably provided so that the minimum application area of the adhesive of 5 mm is at least secured.

[Construction Materials of the Interlabial Pad with the Flap Portions]

<Water-Permeable Sheet>

Materials that are liquid hydrophilic and do not apply stimulus to wearer's skin are used for water permeable sheets provided at the body side face of the inter-labia pad. They include nonwoven fabrics used alone or in combination manufactured by methods such as melt blown spun bond, point bond, through air, needle punch, wet spun lace, foam film, and the like.

The material for the fibrous sheet may be a single kind of fiber or a combination of plural kinds of fibers selected from a mono fiber or a conjugated fiber of core-sheath structure such as those of rayon, acetate, cotton, pulp, synthetic resins.

Among the materials, considering the liquid mobility from the inner face of the labia, chemical stimulation by an activator, and adhesion with the inner wall of the labia, it is preferable to laminate rayon with 1.1 to 4.4 dtex fineness and 7 to 51 mm fiber length by 40 to 80% of a total specific weight per unit area on the body face side, and to laminate a mixture of rayon with 1.1 to 4.4 dtex fineness and 7 to 51 mm fiber length by 14 to 42% of a total specific weight per unit area and PET with 1.1 to 4.4 dtex fineness and 7 to 51 mm fiber length by 6 to 18% of a total specific weight per unit area on the garment face side. After laminating them so that the total specific weight per unit area of the two layers becomes 20 to 60 g/m$^2$, the fibers are entangled by water flow interlacing treatment and then dried to prepare spun lace nonwoven fabric with the thickness of 0.13 to 0.50 mm. The spun lace nonwoven prepared as described is preferable. At this time, by mixing PET on the garment face side, bulkiness can be easily maintained even if the water permeable sheet becomes wet. Therefore, adhesion to the inner wall of the labia can be maintained.

<Absorbent Body>

Materials usable for the absorbent body contained in the inter-labia pad include pulp, chemical pulp, rayon, acetate, natural cotton, water-absorbent polymer, fibrous water-absorbent polymer, synthetic fiber. They may be used alone or as a mixture of two or more. A mixture blended as required is made into a sheet by technologies such as pressure bonding by embossing, lacing by needling well known in the art. The sheets may be adjusted by bulkiness adjustment, layering, folding, etc. as required.

Materials for the sheet can be handled as a sheet or a powder. Their usages are not limited.

It is preferable for the absorbent body, although any material can be used as long as it is capable of absorbing and holding liquid (body fluid), to be bulky, hard to be deformed, less chemically stimulant, and highly flexible to fit into the labia. Specifically, a nonwoven sheet in which, 50 to 150 g/$m^2$ of pulp selected from the range of the fiber length of 1 to 10 mm is laminated on the garment face side and, on the body face side, 150 to 250 g/$m^2$ of a mixture obtained by mixing 60 to 90% of rayon with 1.1 to 4.4 dtex fineness and 20 to 51 mm fiber length with 40 to 10% of natural cotton by this mixing ratio is laminated, which then to be formed into a sheet by dotted embossing to have 2 to 10 mm bulkiness, and more preferable to have 3 to 5 mm bulkiness. Thereby, liquid can be easily transferred from the body face side to the garment face side resulting in the improvement of the absorbing and holding capacity. Furthermore, by providing, on the body side face of the pulp layer, a mesh spun lace nonwoven fabric of rayon with 1.1 to 4.4 dtex fineness and 25 to 51 mm fiber length by a specific weight per unit area of 15 to 40 g/$m^2$, the liquid transferred from the body face side can be diffused by the mesh spun lace to be induced to almost all over the region of the pulp layer. Therefore, more liquid can be effectively absorbed.

<Water-Impermeable Sheet>

Materials that prevent menstrual blood retained in the absorbent body from leaking out of the interlabial pad can be used for water impermeable sheets. Further, if they are moisture permeable materials, it is possible to reduce humidity and unpleasantness when the interlabial pad is worn.

Such materials include, for example, a sheet film where a synthetic resin is transformed into a membrane, an air-permeable film made by being filled with an inorganic filler and processed to be expanded, a laminated material made of a paper or an unwoven fabric and a film, an air-permeable and liquid-impermeable sheet having pore area rate of 10 to 30% and porous diameter of 0.1 to 0.6 mm made by arranging capillaries to be headed towards the absorbent body, etc.

Further, when considering flexibility not deteriorating wear feeling, for example, a film having a specific weight per unit of 15 to 30 g/$m^2$ composed mainly of low density polyethylene (LDPE) having a density of 0.900 to 0.925 g/$cm^3$ is more preferably used. More preferably, the film is emboss processed to reduce contact ratio and friction resistance by providing convex bosses in order to reduce a risk that the interlabial pad falls off from the labia due to a large friction caused by contact with other impermeable sheets, pads used at the same time, underwear, etc. when the interlabial pad is fixed to the inter-labia space.

<Flap Portion and Mini-Sheet Piece (Including the One where a Part of it is the Flap Portion)>

Materials that are the same as the water permeable sheets or the water impermeable sheets may be used for the flap portions and the mini sheet piece. However, materials with elasticity are preferably used for the flap portions.

Basically, materials with elasticity include: for example, synthetic rubbers such as styrene-ethylene-butadiene-styrene block copolymers (SEBS), styrene-isoprene-styrene block copolymers (SIS), urethane; etc., films made from amorphous olefin resins having a density selected from 0.88 to 0.900 g/$cm^3$, porous foam films, nets, and the like. Further, a woven fabric and a fabric to which a fiber spinning filament made from a synthetic rubber is woven into can be also used. Further, a spun bond nonwoven fabric and a melt blown nonwoven fabric composed mainly of a synthetic rubber and a foamed sheet can be used.

Considering flexible feeling when the interlabial pad worn, a porous foam film made from styrene-ethylene•butadiene-styrene block copolymer (SEBS) adjusted in the range of thickness from 15 to 40μ, hole area from 0.28 to 1.77 $mm^2$, hole area rate from 40 to 70% is preferably used.

Nonwoven fabrics may include spun lace nonwoven fabrics whose fibers are intermingled by water pressure and which is made from a conjugated synthetic fiber such as PE/PP, PE/PET, PP/PP having thermal shrinkage property and a sheath-core configuration that a sheath component is made of material with a low melting point and a core component is made of material with a high melting point; a shrink type nonwoven fabric whose fiber is re-treated with a hot-blow processing so that fiber shrinkage is accelerated; a so called extensible spun bond that is processed by force with tentering in the longitudinal direction after continuous long fibers are processed with heat seal so as to be made into a sheet.

More specifically, preferable materials rich in flexibility and drape feeling include shrink type nonwoven fabrics made from compound synthetic fiber such as PE/PP, PE/PET, PP/PP with denier in the range from 1.1 to 4.4 dtex and the length in the range from 7 to 51 mm, having thermal shrinkage property and sheath portion of lower melting point than the core component and 10 to 60 g/$m^2$ by a specific weight per unit. Further, laminated types of the materials can be also used.

Materials without extensity applied with extensity before use included: among nonwoven fabrics, through air nonwoven fabrics made from complex synthetic fibers such as PE/PP, PE/PET, PP/PP having thermal shrinkage property, wherein core component has a high melting point and the sheath component has a lower melting point; spun lace nonwoven fabrics wherein fibers are entangled by water pressure; spun bond nonwoven fabrics transformed into a sheet by layering continuous fibers; needle punch nonwoven fabrics wherein fibers are entangled to one another by needles; SMS nonwoven fabrics wherein spun bond and melt blown are layered in multiple layers to form a sheet; porous foam films; films mainly composed of PE resins and the like. They may be used either alone or in combination of two or more.

Further, it is also possible to apply extensity to the materials by corrugate processing where materials are fit between the male and female die and a shape is embossed by heat, temperature and pressure. More specifically, through-air nonwoven fabrics composed mainly of conjugated synthetic fibers having denier of 1.1 to 4.4 dtex and a specific weight per unit of 10 to 60 g/$m^2$, corrugated so that they can extend in the lateral direction are preferred. Preferable corrugate processing is that male and female dies are provided so that extensity is preferably obtained in the range of at least 10% or more, more preferably, 20 to 50%, still further preferably, the load has a behavior of 0.01 to 0.05N/ 25 mm of loads when 30% extended (test condition: Tensilon tensile tester, speed, 100 mm/min, chuck interval, 100 mm). Other methods to apply extensity include cut lines, circular cutouts.

<Adhesives>

Adhesives usable for the flap portion include gel adhesives, etc. composed of a water-soluble polymer, a crosslinking agent, a plasticizer, water. More specifically, examples of water soluble polymers usable herein include: gelatin, sodium polyacrylic acid, polyvinyl alcohol, carboxymethyl cellulose, etc. Examples of crosslinking agents include water-soluble metal salts such as calcium chloride, magnesium sulfate. Examples of plasticizers include glycerin, wax, paraffin, etc.

Besides them, it is possible to use a so-called pressure-sensitive hot melt as an adhesive agent to form the adhesive portion. Examples of the pressure sensitive hot melt include those obtained by incorporating a tackifier resin such as a rosin-based resin, terpene-based resin; and plasticizers such as a wax in a main synthetic rubber resin such as SIS, SBS, SEBS, styrene-ethylene•propylene-styrene block copolymers (SEPS) as a main component.

Further, it is also possible to use silicon resin adhesives. Example of silicon resin adhesives include mixtures composed mainly of silicon resins and fluorocarbon resins, blended with crosslinking agents made from metal salts such as platinum, molybdenum, antimony; plasticizers such as ester waxes, glycerin, machine oils.

A pressure sensitive hot melt is preferably used if application stability is also considered. More specifically, examples of heat sensitive hot melt adhesives with higher application stability include the one where SEBS, a styrene block copolymer of 15 to 25% by weight, a plasticizer of 15 to 35% by weight and a tackifier of 40 to 70% by weight are melted and blended. An antioxidants, a fluorescence inhibitor, etc. of 0.1 to 1.0% by weight may be added to this kind of heat sensitive hot melt adhesives.

Furthermore, with regard to the adhesives, it is possible to prevent adhesives from being broken and separated off during storage by coating the adhesive area with a sheet of tissue paper (generally available separate paper) coated with silicon or a film sheet coated with a silicon resin.

[Structure of the Interlabial Pad Provided with Biodegradability, Water Dispersibility and Water Solubility]

Preferably the interlabial pad with the flap portions is comprised of a material of biodegradable and/or a material of water dispersible and/or a material of water-soluble. After using the interlabial pad with the flap portions comprised of these materials, it can be disposed into a toilet to flush, thereby the destruction of the pad can be easily and sanitarily achieved and the garbage in a toilet can be decreased.

In this Specification, "biodegradability" means that a substance is decomposed into gas such as carbon dioxide or methane, water, and biomass under anaerobic or aerobic condition according to the natural process under the existence of bacteria represented by actinomycetes and other microbes, and also means that the biodegradability (biodegradable rate and biodegradable degree) of the substance equals to a material naturally generated such as fallen leaves or a synthetic polymer generally recognized having the same biodegradability under the same environment. "Water dispersibility" means the same as water degradability, where there is no effect from the limited amount of water (menstrual blood) upon use, whereas in conditions of large amounts of water or under water flow, the fibers are easily dispersible into at least small pieces which cannot clog the toilet plumbing. "Water solubility" means the property of not being affected by limited amount of water (menstrual blood) upon use, but being soluble in large amounts of water or under a flow of water.

<Water-Permeable Sheet>

Materials that can be used for water permeable sheets include: wet spun lace nonwoven fabrics with fiber length selected from 1 to 15 mm as well as spun lace nonwoven fabrics. Other materials include hydrolyzed biodegradable resins such as polylactic acids, polybutylene succinate. Examples usable herein include melt blown nonwoven fabrics made from polylactic acids having a specific weight per unit of 20 to 60 $g/m^2$ and spun bond nonwoven fabrics having a specific weight per unit of 15 to 30 $g/m^2$ and denier of 1.1 to 3.3 dtex. Materials for nonwoven fabrics may or may not be applied with pore opening treatment.

For other materials, it is possible to use acetate or a single synthetic fiber alone, or a tow that is a continuous fiber composed of laminated bodies by adjusting it in the range of 50 to 300 $g/m^2$ by a specific weight per unit and fibrillating fibers thereof.

<Absorbent Body>

Nonwoven fabric sheets obtained by needling can be used for absorbent bodies.

It is desirable to use carboxymethyl cellulose fibers considering biodegradability of polymer absorbent materials.

<Water Impermeable Sheet>

As material that can be used for water impermeable sheet, a PVA film, a PVA film sheet having one or both sides or a part thereof treated with water-repellent such as silicon, PVA films mixed with silicone, a starch film, a laminated paper laminated with a tissue and a film made from biodegradable resins by hydrolyzation such as polylactic acids, polybutylene succinates, etc. can be used. If required, 0.1 to 5% of inorganic pigments may be mixed to color.

It is desirable to use laminated papers where films made from polylactic acids are laminated with thickness of 10 to 20μ with tissues selected from the range of 15 to 20 $g/m^2$ by a specific weight per unit and further composite area ratio when laminated being 5 to 40% considering maintenance of leakage resistance under hyper humidity and lower loads to septic tanks.

<Flap Portion and Mini Sheet Piece (Including the One where a Part of it is the Flap Portion )>

Materials usable for the mini sheet piece include: films, spun bond nonwoven fabrics, melt blown nonwoven fabrics, etc. made from biodegradable materials such as polylactic acids; polybutylene succinate; films and nonwoven fabrics, etc. made from insoluble materials such as PVA, CMC; water dispersible tissues, spun lace nonwoven fabrics, etc. composed mainly of cellulose fibers, recycled cellulose fibers, etc.

Preferably, of these, spun bond nonwoven fabrics or melt blown nonwoven fabrics composed mainly of biodegradable materials that are made into sheets whose fineness is adjusted to the range from 0.1 to 3.3 dtex, a specific weight per unit is adjusted to the range of 15 to 40 $g/m^2$, obtained from the mechanical corrugate processing are preferred.

<Bonding Methods>

Bonding methods include: bonding with polyvinyl alcohol, etc. with water solubility or water swellingness, heat seal bonding, hydrogen bonding, etc. They are used alone or two or more of them are used at the same time.

[Wrapping Body]

Individual wrapping method for the interlabial pad with the flap portions of the present invention now will be explained.

<Wrapping Method>

Figure 21:
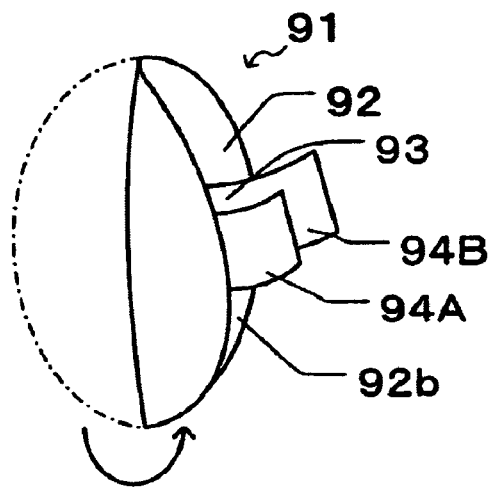
FIGS. 21A–C illustrate a process chart showing the process that the interlabial pad with the flap portions is wrapped in the wrapping container that is made by folding the wrapping sheet in half to form the wrapping body.
Figure 21:
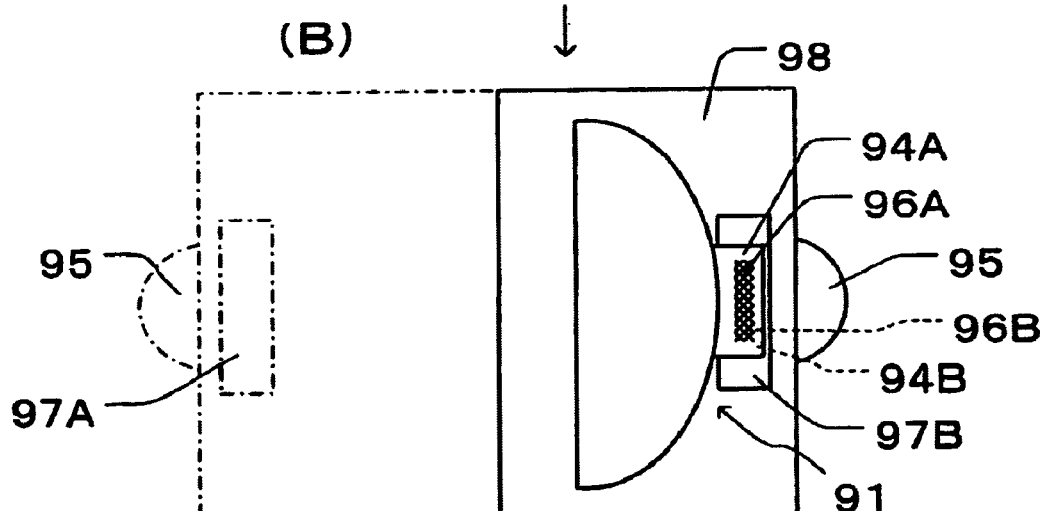
Figure 21:
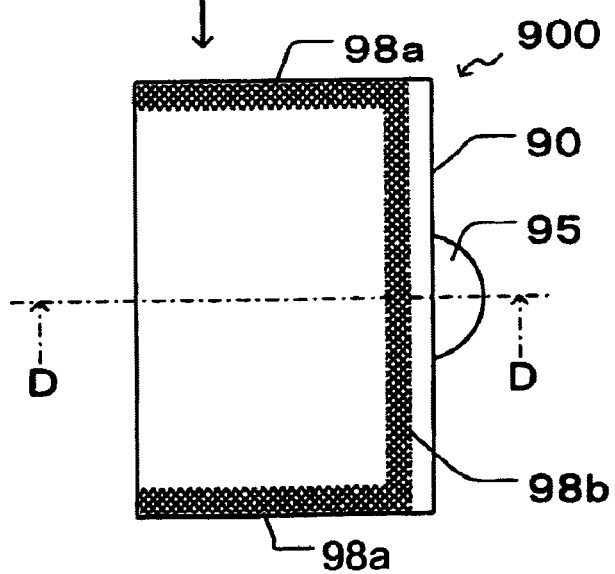
Figure 22:
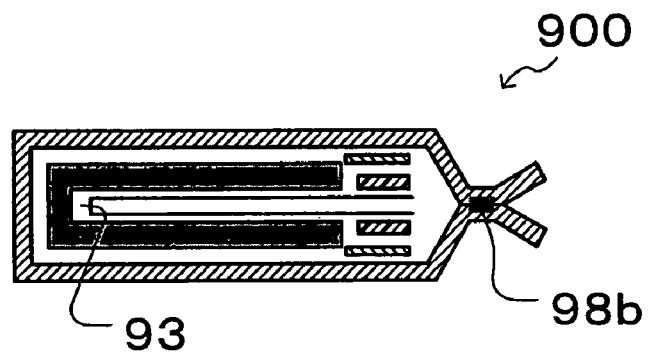
FIG. 22 is a cross section D—D of the wrapping body in FIG. 21(C).
Figure 23:
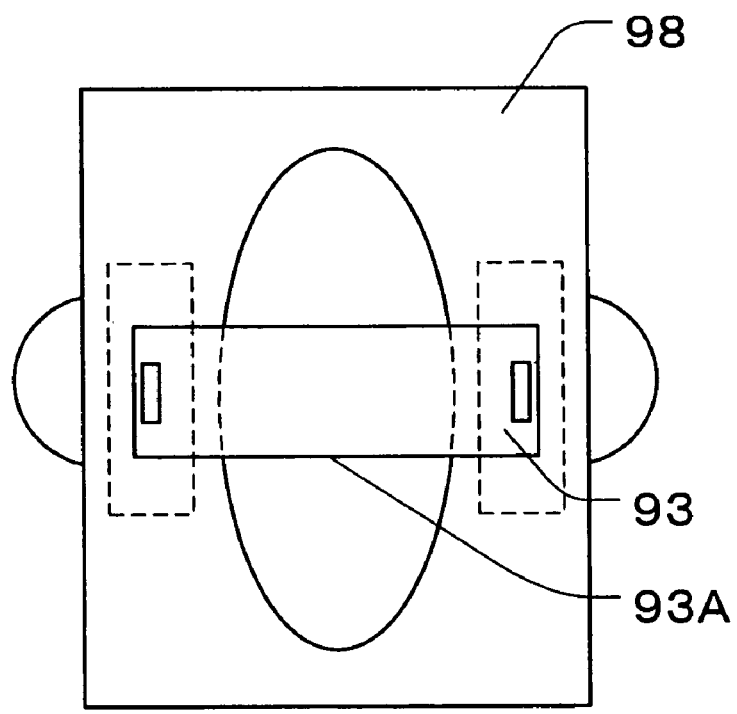
FIG. 23 is a view showing the state that the wrapping body in FIG. 21(C) is unsealed.
Figure 24:
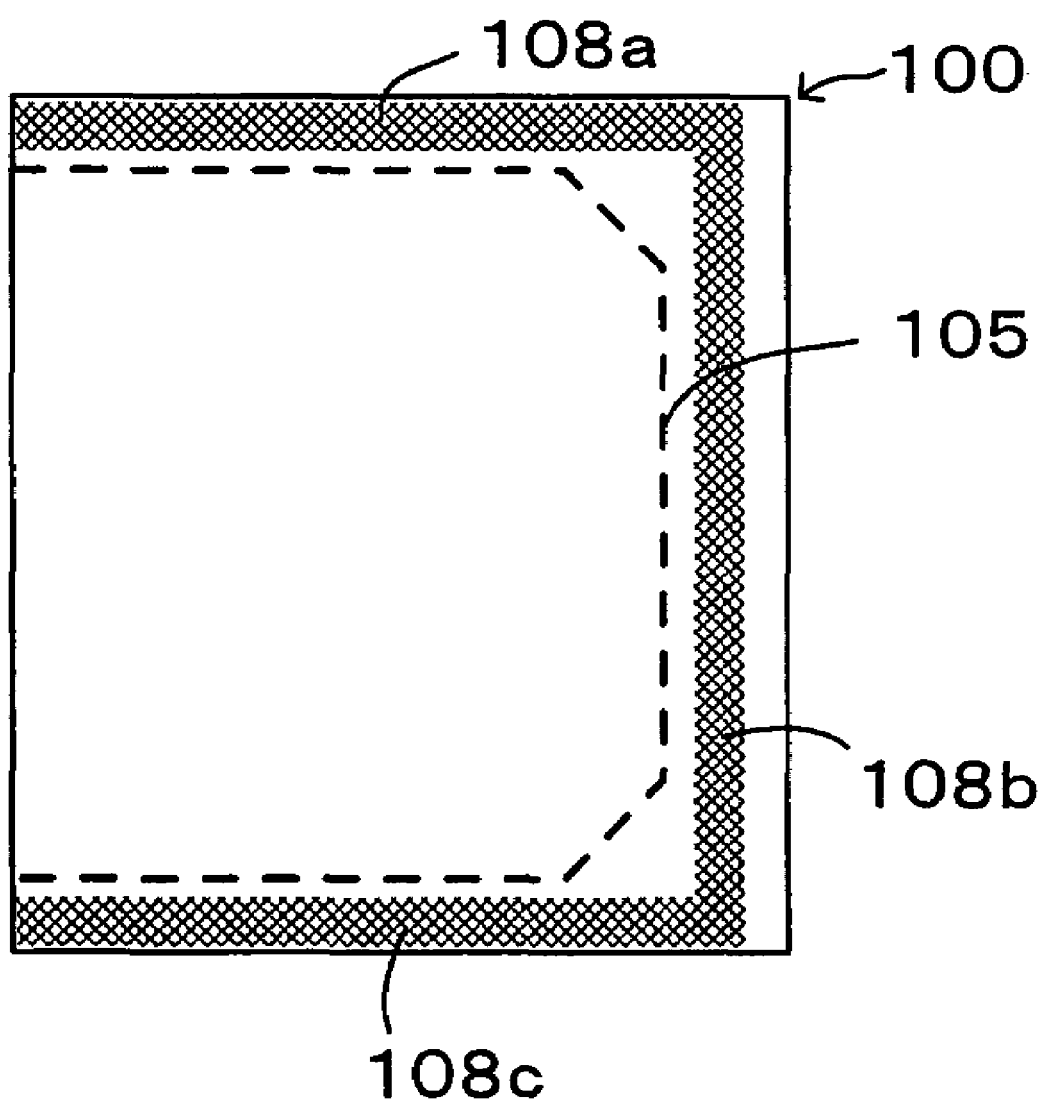
FIG. 24 is a view showing a wrapping container that can be unsealed with a broken line.
Figure 25:
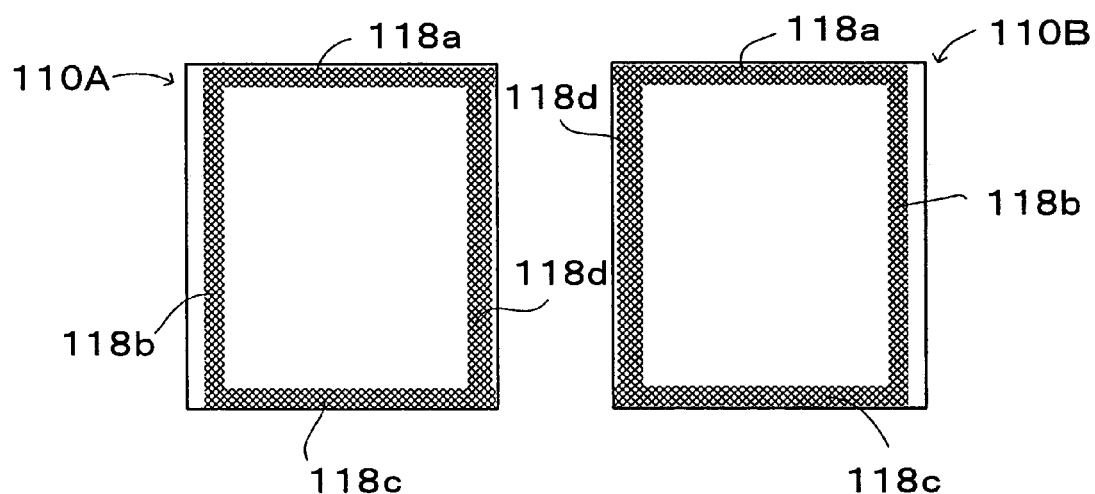
FIGS. 25A–B illustrate a view showing a wrapping container constituted of the two wrapping sheets.
Figure 25:
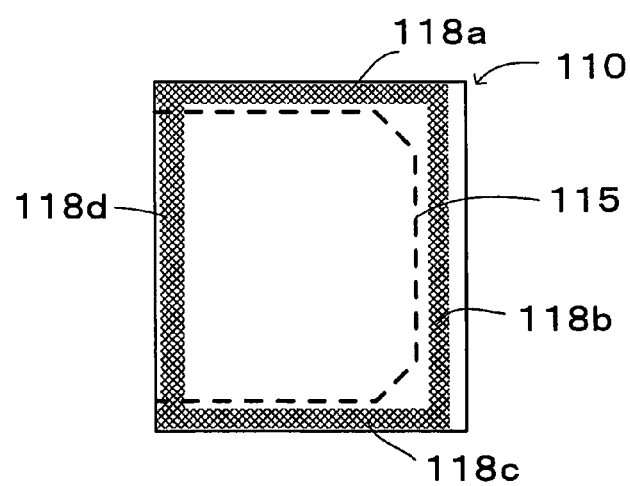

With regard to the wrapping method to wrap the interlabial pad with the flap portions in the wrapping container, shown in the first and the second embodiments, the wrapping sheet may be folded in two or three, or multiple wrapping sheets may be glued together. FIG. 21 is a process chart showing the process that the interlabial pad with the flap portions 91 is wrapped in the wrapping container 90 that is made by folding the wrapping sheet 98 in half to form the wrapping body 900. FIG. 22 is a cross section C—C of FIG. 21(C). FIG. 23 is a view showing the state that the wrapping body 90 is unsealed. FIG. 24 is a view showing a wrapping container 100 that can be unsealed with a broken line. FIG. 25 is a view showing a wrapping container 110 constituted of the two wrapping sheets.

As shown in FIG. 21(A), fold the interlabial pad with the flap portions 91 along the longitudinal axis in such a way that the left and right side edges of the interlabial pad 92 face to each other. In this case, the opposite side face to the body side face 92b to which the mini-sheet piece 93 is attached face inward. Then, as shown in FIG. 21(B), put the interlabial pad with the flap portions 91 on the right side of the wrapping sheet 98 attached with the tab 95. In this case, the adhesive 96B applied on the flap portion 94B that is positioned on the other side of the flap portion 94A should be positioned on the separate sheet 97B. By this, the interlabial pad 91 is re-separably attached to the wrapping sheet 98. And, fold the wrapping sheet 98 in half along the longitudinal axis to wrap the interlabial pad with the flap portions 91.

Then, as shown in FIG. 21(C), provide the bonding section 98a, 98b and 98c bonded by heat seal at the overlapped regions where margins of wrapping sheet 98 are overlapped to each other and bond them to make the wrapping body 900. The bonding strength of the bonding section 98a, 98b and 98c should be adjusted so that a separation strength of 0.03 to 0.2N/25 mm is obtained with Tensilon tensile tester, pulling speed 100 mm/min, chuck interval, 100 mm in order to prevent break during use.

In this case, the tab 95 should not be bonded. The tab 95 shows the wearer the unsealing position of the wrapping container 90, as well as makes unsealing easy. By keeping two tabs 95 not bonded, the wearer grasps and pulls the tabs 95 towards opposing directions to unseal the wrapping container 90 easily.

Inner structure of the wrapping body 900 is that, as shown in FIG. 22, the mini-sheet piece 93 is provided at the position opposed to the bonding section 98b that is to be the unsealing opening. So, as shown in FIG. 23, the mini-sheet piece 93 is exposed immediately after unsealing. The wearer can find the finger insertion opening 93A without turning over the wrapping sheet 98 and insert her finger therein.

The wrapping container may be unsealed by separating off the bonding section by heat seal etc., or by breaking a part of the wrapping container along the broken line provided at the inner edge of the bonded section. For example, as shown in FIG. 24, the wrapping container 100 can be unsealed by cutting the edge of the wrapping container 100 along the broken line 105 if it is provided on the inward side of the bonded sections 108a, 108b and 108c.

Further, as the wrapping container 110 shown in FIG. 25, two warpping sheets 110A and 110B are prepared so that the interlabial pad with the flap portions (not shown) may be preliminarily sandwiched between the wrapping sheets and that the wrapping sheets 110A and 110B may be glued together at four bonding portions 118a, 118b, 118c and 118d to laminate both. In this case, the broken line 115 is provided at the inner side of the bonded sections 118a, 118b and 118c.

This type of broken line can surely guide the direction of separating off preventing dirt from entering. Specifically, the length of the perforation is preferably 0.5 to 5 mm, the width is preferably 3 mm at maximum. The length of non-perforated region is preferably 0.5 to 3 mm. Furthermore, the bonding strength of the bonding section is preferably enhanced so that cannot be unsealed easily in order to reduce mis-opening.

The broken line may end at the other side edge or at the middle point of the longitudinal direction so long as it starts at least from one end edge of the wrapping container in the longitudinal direction. The breaking strength in the lateral direction is, preferably 0.05 to 1.5N/25 mm, more preferably 0.1 to 1.0N/25 mm at the pulling condition of 25 mm width, 100 mm/minute.

Further, it is possible to adopt measures such as printing an arrow or the like so that the wearer can easily locate the starting point of the broken line; applying a different cut near the starting point (for example, round edge, etc) from a cut at the ending point; forming the wrapping container in such a way that the width gets larger towards the starting point of perforation so that the wearer grasps the narrower side; and so on.

<Materials of the Wrapping Container>

Materials known in the art can be used for the sheet used in the wrapping container. Examples usable herein include: polyethylene, polyrulopyrene polyester, polyvinyl alcohol, polylactic acids, polybutylene succinate, nonwoven fabrics, paper and laminated materials thereof with thickness of 15 to 60 micron.

More specifically, considering a shielding feature to prevent dusts or dirt from entering and retention of wrapping shape, a conjugated nonwoven fabric composed of 6 to 10 g/m$^2$ of spun bond, 5 to 20 g/m$^2$ of melt blown, and 6 to 10 g/m$^2$ of spun bond; or a film prepared in 15 to 30 micron in thickness which is mainly composed of LDPE having density selected from 0.9 to 0.925 g/cm$^3$; or the like may be used.

Biodegradability, water dispersiveness and water solubility are created by altering the composition of biodegradable or water-soluble polylactic acid, polybutylene succinate, polyvinyl alcohol, etc. in the synthetic resin composition.

[Usage Information Service]

It is desirable to offer usage information of the interlabial pad with the flap portions according to the present invention in order to prevent the wearers from misunderstanding the fixing method.

In this respect, for example, the case that the wearer may use the interlabial pad with the flap portions in an incorrect way includes that the wearer tries to put the interlabial pad in an orthogonal direction to her vulvar cleft; and that the wearer tries to insert the interlabial pad into the ostium vaginae in the vertical direction like a tampon; and that the wearer fixes the interlabial pad inside out; and that the wearer puts the interlabial pad on a surface of a concomitantly-used sanitary napkin without insert it between the labia; and so on. These misuses may significantly deteriorate wear feeling, excessively induce leakage of menstrual blood, and cause removal of the interlabial pad from the wearer's crotch.

It is desirable to pass on correct information about the interlabial pad with the flap portions of the present invention to users to achieve enough effect and clearly show wearers the usage for correct fixing and handling quickly.

The methods to pass on usage information to users include: enclosing an explanatory leaflet in the package, printing usage on the individual wrapping container, putting descriptions of the item and usage in associate magazines, putting usage in the homepage, displaying directions for use on the showcase in the market, enclosing an explanatory leaflet in the product package of free samples, posting an instruction in powder rooms, verbal explanation at customer affairs, etc. Most desirable method among them is that a wearer can make certain of usage every time she uses the product such as enclosing an explanatory leaflet in the packaging, printing on the individual wrapping container.

INDUSTRIAL APPLICABILITY

According to the present invention, it is possible to affix the flap portions provided at the side edges of the interlabial pad to the labia majora when fixing the interlabial pad. So, even when the interlabial space the interlabial pad received a large quantity of body fluid, the interlabial pad can remain at the original without causing positional displacement. This prevents a gap from being generated between the labia and the interlabial pad and body fluid from leaking.

What is claimed is:

1. A wrapping body comprising;
an interlabial pad having longitudinal and lateral directions appropriate for insertion between the labia of a wearer, an interlabial pad body for absorbing body fluid, and a pair of flap portions provided on the interlabial pad body to extend beyond the side edges of the interlabial pad body in the lateral direction,
wherein said interlabial pad body has a surface side sheet disposed on the body side for contacting the skin of the wearer and a backside sheet disposed opposite to the surface side sheet, and the surface side sheet and the backside sheet are bonded together at the peripheral edges thereof to enclose an absorbent body for absorbing said body fluid,
wherein the pair of the flap portions is provided with a surface for contacting the skin of the wearer, and said surface has an adhesive portion,
the pad comprising a mini-sheet piece which forms a finger insertion opening having a finger breadth opening secured and a finger insertion space continuing therefrom,
wherein the mini-sheet piece is attached to an opposite side face to a body side face of the interlabial pad body,
the wrapping body comprising a wrapping container that wraps the interlabial pad,
wherein the flap portions provided on the interlabial pad are temporarily fixed detachably to an inner face of the wrapping container, and
wherein the interlabial pad is folded and contained such that the finger insertion opening opens when the wrapping container is unsealed.

2. The wrapping body comprising:
an interlabial pad;
a wrapping container that contains the interlabial pad;
the interlabial pad having longitudinal and lateral directions appropriate for insertion between the labia of the wearer comprising an interlabial pad body for absorbing body fluid and a pair of flap portions provided on the interlabial pad body to extend beyond the side edges of the interlabial pad body in the lateral direction,
wherein said interlabial pad body has a surface side sheet disposed on the body side for contacting the skin of the wearer and a backside sheet disposed opposite to the surface side sheet, and the surface side sheet and the backside sheet are bonded together at the peripheral edges thereof to enclose an absorbent body for absorbing said body fluid,
wherein the pair of the flap portions is provided with a surface for contacting the skin of the wearer, and said surface has an adhesive portion,
wherein the pair of flap portions provided on the interlabial pad is temporarily fixed detachably to an inner face of the wrapping container,
wherein the wrapping container comprises a plurality of wrapping sheets sandwiching the interlabial pad, and
wherein the inner face to which the flap portions are temporarily fixed comprises an inner portion of a face having both side edges to form the overlapped portion.

* * * * *

UNITED STATES PATENT AND TRADEMARK OFFICE
CERTIFICATE OF CORRECTION

| | | |
|---|---|---|
| PATENT NO. | : 7,033,342 B2 | Page 1 of 1 |
| APPLICATION NO. | : 10/705670 | |
| DATED | : April 25, 2006 | |
| INVENTOR(S) | : Satoshi Mizutani et al. | |

It is certified that error appears in the above-identified patent and that said Letters Patent is hereby corrected as shown below:

TITLE PAGE, ITEM (30)
The Foreign Application Data has been omitted. Please insert:

May 22, 2001    (JP).......................2001-152403

October 11, 2001 (JP).......................2001-314176

Signed and Sealed this

Twenty-fifth Day of July, 2006

JON W. DUDAS
*Director of the United States Patent and Trademark Office*